US012331732B2

(12) United States Patent
Herve et al.

(10) Patent No.: US 12,331,732 B2
(45) Date of Patent: Jun. 17, 2025

(54) SIMULATED RESPIRATORY TRACT

(71) Applicant: PHILIP MORRIS PRODUCTS S.A., Neuchatel (CH)

(72) Inventors: Pierre Herve, Daillens (CH); Shoaib Majeed, Neuchatel (CH); Sandro Steiner, Schonbuhl (CH)

(73) Assignee: Philip Morris Products S.A., Neuchatel (CH)

( * ) Notice: Subject to any disclaimer, the term of this patent is extended or adjusted under 35 U.S.C. 154(b) by 1526 days.

(21) Appl. No.: 16/631,312

(22) PCT Filed: Jul. 13, 2018

(86) PCT No.: PCT/EP2018/069091
§ 371 (c)(1),
(2) Date: Jan. 15, 2020

(87) PCT Pub. No.: WO2019/016094
PCT Pub. Date: Jan. 24, 2019

(65) Prior Publication Data
US 2020/0209219 A1    Jul. 2, 2020

(30) Foreign Application Priority Data
Jul. 17, 2017 (EP) .................................... 17181667

(51) Int. Cl.
*F04B 39/10* (2006.01)
*A61M 16/00* (2006.01)
(Continued)

(52) U.S. Cl.
CPC ......... *F04B 39/10* (2013.01); *A61M 16/0057* (2013.01); *A61M 16/006* (2014.02);
(Continued)

(58) Field of Classification Search
CPC ...... F04B 39/0016; F04B 25/00; F04B 39/10; F04B 41/06; A61M 16/20;
(Continued)

(56) References Cited

U.S. PATENT DOCUMENTS 4,167,070 A    9/1979 Orden
5,370,504 A *  12/1994 Nagashima ............. F04B 27/02
                                                  417/523
(Continued)

FOREIGN PATENT DOCUMENTS

CN    103366625    10/2013
DE    197 13 636    10/1998
(Continued)

OTHER PUBLICATIONS

Office Action issued in Russia for Application No. 2021123668 dated Jun. 6, 2023 (14 pages). English translation included.
(Continued)

*Primary Examiner* — Peter J Bertheaud
(74) *Attorney, Agent, or Firm* — Mueting Raasch Group

(57) ABSTRACT

There is described herein a system for determining the interaction between a test atmosphere and a simulated respiratory tract, said system comprising: (a) a first pump comprising: (i) a chamber configured for containing a first volume of gas comprising a test atmosphere; (ii) a first port adapted for receiving and outputting gas and comprising a valve for regulating the flow of gas through the first port, said valve being moveable between open and closed positions, wherein in the open position said valve is openable towards a test atmosphere or surrounding air; (iii) a second port adapted for outputting and receiving gas and comprising a valve for regulating the flow of gas through the second port, said valve being moveable between open and closed positions; (iv) a piston plate in the chamber, said piston plate (Continued)

comprising one or more apertures for the uptake or inflow of gas into the chamber wherein one or more, or each, of the apertures include a valve that is movable between open and closed positions and is capable of regulating the uptake or inflow of gas; (b) a second pump comprising: (i) a chamber configured for containing a second volume of gas, wherein the first and second volumes of gas are different; (ii) a port adapted for receiving and outputting gas; and (iii) a motor for controlling the operation of the second pump; (c) a connecting structure operable to transmit the gas from the first pump into the second pump; and (d) one or more openings in the first pump or the second pump or the walls of the connecting structure or a combination of two or more thereof, said openings being capable of receiving a module for containing a cell culture medium or for monitoring conditions in the chamber or for gas sampling or for gas characterisation.

10 Claims, 3 Drawing Sheets

(51) Int. Cl.
*F04B 25/00* (2006.01)
*F04B 39/00* (2006.01)
*F04B 41/06* (2006.01)
*G09B 23/28* (2006.01)
*G09B 23/30* (2006.01)
*G09B 23/32* (2006.01)

(52) U.S. Cl.
CPC ......... *A61M 16/0072* (2013.01); *F04B 25/00* (2013.01); *F04B 39/0016* (2013.01); *F04B 41/06* (2013.01); *G09B 23/288* (2013.01); *G09B 23/30* (2013.01); *G09B 23/32* (2013.01); *A61M 2016/0027* (2013.01); *A61M 2205/3368* (2013.01)

(58) Field of Classification Search
CPC .......... A61M 16/0057; A61M 16/0072; A61M 16/0069; A61M 2205/3368; A61M 2016/0027; G09B 23/32; G09B 23/288; G09B 23/30
See application file for complete search history.

(56) References Cited

U.S. PATENT DOCUMENTS

| | | | |
|---|---|---|---|
| 5,484,270 | A | 1/1996 | Adahan |
| 5,597,310 | A | 1/1997 | Edde |
| 6,106,479 | A | 8/2000 | Wunderlich |
| 2007/0065785 | A1 | 3/2007 | Wenske |
| 2016/0217709 | A1 | 7/2016 | Minskoff |
| 2018/0216058 | A1 | 8/2018 | Hu |

FOREIGN PATENT DOCUMENTS

| | | |
|---|---|---|
| DE | 102010027436 | 7/2011 |
| EP | 1 431 746 | 6/2004 |
| JP | S60-107872 | 7/1985 |
| JP | H08-317979 | 12/1996 |
| JP | 2006-021061 | 1/2006 |
| JP | 2008-152152 | 7/2008 |
| JP | 2017-158809 | 9/2017 |
| RU | 69518 U1 | 12/2007 |
| RU | 126703 | 4/2013 |
| SU | 214732 | 6/1968 |
| SU | 321841 | 11/1971 |
| WO | WO 2003-031946 | 4/2003 |
| WO | WO 2013/064503 | 5/2013 |
| WO | WO 2014/018703 | 1/2014 |
| WO | WO 2015-082666 | 6/2015 |
| WO | WO 2016/022722 | 2/2016 |
| WO | WO 2016/118935 | 7/2016 |
| WO | WO 2018/075543 | 4/2018 |
| WO | WO 2019/016094 | 1/2019 |

OTHER PUBLICATIONS

Office Action issued in Japan for Application No. 2021-538219 dated Dec. 21, 2023 (9 pages). English translation included.
PCT International Search Report and Written Opinion for Application No. PCT/EP2020/050725 dated Jun. 17, 2020 (18 pages).
Extended European Search Report for Application No. 19151940.4 dated Sep. 23, 2019 (16 pages).
Nigam et al., "Enzyme Based Biosensors for Detection of Environmental Pollutants—A Review", *J. Microbial. Biotechnol.* (2015) 25(11), 1773-1781.
Robinson et al., "3D Airway Reconstruction Using Visible Human Data Set and Human Casts with Comparison to Morphometric Data", *The Anatomical Record*, 292:1028-1044 (2009).
Routkevitch et al., "Nanostructured Gas Microsensor Platform", NSTI—Nanotech 2005, www.nsti.org, ISBN 0-9767985-1-4, vol. 2, 2005.
Zhang et al., "Airflow and Nanoparticle Deposition in a 16-Generation Tracheobronchial Airway Model", *Annals of Biomedical Engineering*, vol. 36, No. 12, Dec. 2008.
Zopf et al., "Bioresorbable Airway Split Created with a Three-Dimensional Printer", *The New England Journal of Medicine*, 368;21, May 23, 2013, pp. 2043-2045.
Office Action issued in Japan for Application No. 2020-501489 dated Jun. 22, 2022 (4 pages). English translation included.
Extended European Search Report for Application No. 17181667.1 dated Apr. 13, 2018 (6 pages).
PCT International Search Report and Written Opinion for Application No. PCT/EP2018/069091 dated Nov. 6, 2018 (14 pages).
Lin et al., "The Application of Engineered Liver Tissues for Novel Drug Discovery", *Expert Opin. Drug Discov.* (2015) 10, 519-540.
Muller et al., "Culturing of Human Nasal Epithelial Cells at the Air Liquid Interface", *J Vis Exp.* (2013) (80): 50646.
Office Action issued in Russia for Application No. 2020106127/03 dated Aug. 30, 2021 (2 pages). English translation included.
Office Action issued in China for Application No. 202080007268.1 dated Dec. 22, 2022 (10 pages). English translation included.

* cited by examiner

SIMULATED RESPIRATORY TRACT

This application is a U.S. National Stage Application of International Application No. PCT/EP2018/069091 filed Jul. 13, 2018, which was published in English on Jan. 24, 2019 as International Publication No. WO 2019/016094 A1. International Application No. PCT/EP2018/069091 claims priority to European Application No. 17181667.1 filed Jul. 17, 2017.

FIELD OF THE INVENTION

The present invention relates to inter alia apparatuses, systems, methods and uses relating to simulating the structure and/or function of a respiratory tract and its breathing behavior. The present invention is useful for investigating interactions between test agents (for example, inhalable agents in test atmospheres) and the respiratory tract. In particular, the present invention is concerned with simulating the human respiratory tract.

BACKGROUND OF THE INVENTION

The respiratory system passes from the nose and upper airway to the alveolar surface of the lungs, where gas exchange takes place. Inhaled aerosols move from the mouth through the upper airway and eventually reach the alveoli. As the aerosol moves more deeply into the respiratory tract, more soluble gases are adsorbed and aerosol particles are deposited deep in the airways and alveoli. One particular aerosol of interest in the context of the present invention is smoke—such as tobacco smoke—as the impact of smoke on or through a simulated respiratory tract can be studied.

Existing aerosol exposure systems most commonly rely on either a continuous, unidirectional aerosol flow or on passive sedimentation. Continuous aerosol flows are generated by positive or negative pressure and the aerosols are directed perpendicularly towards the biological test system or streamed in a direction parallel to the plane of the biological test system. Dose delivery efficiency in this exposure mode is mainly a function of the geometry of the exposure chamber and the flow velocity of the test aerosol. The mouth, breath-hold time and the dynamic flow patterns occurring during human breathing (that is, inhalation and exhalation) cannot be simulated by current aerosol exposure systems however. A dose delivery representative for the in vivo situation, especially the relative delivery of particulate and gaseous aerosol constituents is therefore unlikely to be reached. In addition, the filtering action of the conducting airways cannot be simulated in a representative way. Thus, with current aerosol exposure systems, the same aerosol particle size distribution aerosol is used for instance with bronchial cell cultures and nasal cultures. In living organisms however, larger aerosol particles mainly interact with and are removed from the aerosol in the upper respiratory tract, whereas deeper regions of the respiratory tract, are mainly exposed to the smaller aerosol particle sizes and the gaseous constituents. In addition, in continuous flow exposure systems, aerosol dilution is achieved by continuously adding dilution air to the aerosol upstream in proximity to the exposure chambers. However, if smoking behaviour is to be simulated like in a biological organism, this dilution mode is not representative of the organism because it does not account for a mouth hold-period during which highly dense aerosol is allowed to age for up to several seconds followed by being pulled into the respiratory tract along with a large volume of dilution air.

In passive aerosol sedimentation, a test aerosol is injected into a chamber at the bottom of which the biological test systems are located. Once the aerosol is injected, aerosol is allowed to sediment on the test system, usually by gravitation. Electrostatic attraction of the aerosol particles to the test system may be used to increase aerosol particle deposition. Nano-sized aerosol particles, in particular, may require electrostatic attraction due to their low sedimentation efficiency. Exposures to complex aerosols containing aerosol particles of various sizes and densities as well as gaseous constituents cannot be conducted in passive aerosol sedimentation systems because the differential relative delivery of large aerosol particles, small aerosol particles and gaseous aerosol constituents are not representative of processes occurring in a living organism.

There is a continuing need in the art for improved simulated systems for studying the respiratory tract.

SUMMARY OF THE INVENTION

In a first aspect, there is provided a system for determining the interaction between a test atmosphere and a simulated respiratory tract, said system comprising: (a) a first pump comprising: (i) a chamber configured for containing a first volume of gas comprising a test atmosphere; (ii) a first port adapted for receiving and outputting gas and comprising a valve for regulating the flow of gas through the first port, said valve being moveable between open and closed positions, wherein in the open position said valve is openable towards a test atmosphere or surrounding air; (iii) a second port adapted for outputting and receiving gas and comprising a valve for regulating the flow of gas through the second port, said valve being moveable between open and closed positions; (iv) a piston plate in the chamber, said piston plate comprising one or more apertures for the uptake or inflow of gas into the chamber wherein one or more, or each, of the apertures include a valve that is movable between open and closed positions and is capable of regulating the uptake or inflow of gas; and (v) a motor for controlling the operation of the first pump; (b) a second pump comprising: (i) a chamber configured for containing a second volume of gas, wherein the first and second volumes of gas are different; (ii) a port adapted for receiving and outputting gas; and (iii) a motor for controlling the operation of the second pump; (c) a connecting structure operable to transmit the gas from the first pump into the second pump; and (d) one or more openings in the first pump or the second pump or the walls of the connecting structure or a combination of two or more thereof, said openings being capable of receiving a module for containing a cell culture medium or configured to store a cell culture medium or for monitoring conditions in the chamber or adapted to monitor conditions in the chamber or for gas sampling or adapted to sample gas or for gas characterisation or adapted to characterise gas.

Suitably, the pumps are piston pumps comprising a piston plate and a base.

Suitably, the connecting structure is hollow.

Suitably, the connecting structure is branched.

Suitably, one terminating branch of the connecting structure is joined to the second pump and one or more further terminating branches are joined to a separate pump, each separate pump comprising: (i) a chamber to contain a volume of gas, wherein the volume of gas is the same volume as the second volume of gas in the second pump; (ii)

a port for receiving and outputting gas and for joining to the connecting structure; and (iii) a motor for controlling the operation of the pump.

Suitably, each separate pump is the same as the second pump.

Suitably, the system is contained in a housing, suitably a temperature controlled housing.

Suitably, the temperature of the housing is controlled by a thermostat.

Suitably, the temperature in the housing is about 37° C.

Suitably, the different volumes of the first and second pumps represent the internal volume of different compartments of the respiratory tract, suitably, the human respiratory tract.

Suitably, the volume of the separate pumps represent the internal volume of different compartments of the respiratory tract, suitably, the human respiratory tract.

Suitably, the displacement volume of the first and second pumps is at least as large as the maximally achievable volume uptake in the corresponding compartment of the respiratory tract.

Suitably, the displacement volume of the separate pumps is at least as large as the maximally achievable volume uptake in the corresponding compartment of the respiratory tract.

Suitably, the pumping pressure of the motor or pump can correspond to atmospheric pressure or above or below atmospheric pressure.

Suitably, the displacement volume of the first pump is between about 0 and 100 ml or between about 1 and 100 ml.

Suitably, the displacement volume of the second pump is between about 0 and 4000 ml or between about 1 and about 4000 ml.

Suitably, the pumps comprise stainless steel.

Suitably, the chamber is a cylinder.

Suitably, the chamber comprises glass.

Suitably, the chamber of the first pump has a smaller volume than the chamber of the second pump.

Suitably, the volume of the chamber of the first pump represents the volume of the oral and oropharyngeal cavity.

Suitably, the volume of the chamber of the second pump represents the volume of lung lumen or a part thereof.

Suitably, the volume of the connecting structure represents the volume of conducting airways of the lung, suitably the human lung.

Suitably, the system further comprises a computer controller capable of synchronising the operation of the system.

Suitably, one or more of the first pump or the second pump or the connecting structure comprise one or more modules containing quartz crystal microbalances.

Suitably, the openings in the first pump or the second pump or the walls of the connecting structure are threaded or non-threaded.

Suitably, one or more of the openings contain a module.

Suitably, the one or more modules are adapted to contain a cell culture medium or configured to store a cell culture medium or adapted to monitor conditions in the chamber or adapted to monitor conditions in the chamber or adapted to sample gas or adapted to characterise gas.

Suitably, the modules are located on the base of the piston plate of the first and/or second pump and/or in the walls of the connecting structure.

Suitably, the one or more modules contain a cell culture medium.

Suitably, the cell culture medium comprises or is in contact with a culture of cells, suitably, a 2- or 3-dimensional culture of cells.

Suitably, the modules adapted for containing or storing a cell culture medium further comprise a microfluidic channel and optionally a microfluidic pump connected thereto.

Suitably, the modules are positioned in a horizontal plane in one or more of the first pump or the second pump or the walls of the connecting structure.

Suitably, the connecting structure comprises stainless steel.

Suitably, the chamber of the first pump has a volume of about 100 ml.

Suitably, the chamber of the second pump has a volume of about 1 litre to about 4 litres.

In a further aspect, there is provided a pump for displacing a volume of gas comprising: (i) a chamber configured for containing a volume of gas and comprising a base and one or more openings capable of receiving one or more modules for containing or storing a cell culture medium or for monitoring conditions in the chamber or for gas sampling or for gas characterisation; (ii) a first port for receiving and outputting the gas, when contained in the chamber, and comprising a first valve for regulating the flow of gas through the first port, said first valve being moveable between open and closed positions, wherein in the open position said valve can be opened towards a test atmosphere or surrounding air; and (iii) a second port for outputting and receiving gas, when contained in the chamber, and comprising a second valve for regulating the flow of gas through the second port, said valve being moveable between open and closed positions; and (iv) a piston plate in the chamber, said piston plate comprising one or more apertures for the uptake or inflow of gas into the chamber wherein one or more, or each, of the apertures include a valve that is movable between open and closed positions and is capable of regulating the uptake or inflow of gas.

Suitably, the pump is a piston pump.

Suitably, the one or more openings in the chamber are threaded or non-threaded.

Suitably, the one or more openings comprise a module.

Suitably, the module is threaded or non-threaded.

Suitably, the one or more modules are adapted to contain a cell culture medium or configured to store a cell culture medium or adapted to monitor conditions in the chamber or adapted to monitor conditions in the chamber or adapted to sample gas or adapted to characterise gas.

Suitably, the modules are located on the base of the pump.

Suitably, the one or modules contain a cell culture medium.

Suitably, the cell culture medium comprises or is in contact with a culture of cells, suitably, a 2 or 3-dimensional culture of cells.

Suitably, the modules adapted for containing or storing a cell culture medium further comprise a microfluidic channel and optionally a microfluidic pump connected thereto.

Suitably, the modules are positioned in a horizontal plane in the one or more of the first pump or the second pump or the walls of the connecting structure.

Suitably, the module comprises quartz crystal microbalances.

Suitably, the pump further comprises a motor.

Suitably, the pumping pressure corresponds to atmospheric pressure or above or below atmospheric pressure.

Suitably, the displacement volume of the pump is between about 0 and 100 ml or between about 1 and about 100 ml.

Suitably, the pump comprises stainless steel.

Suitably, the chamber is a cylinder.

Suitably, the chamber comprises glass.

Suitably, the chamber of the pump has a volume of about 100 ml.

In a further aspect there is provided a piston pump for displacing a volume of gas comprising: (i) a chamber configured for containing a volume of gas and containing a piston plate comprising one or more apertures for the uptake or inflow of gas into the chamber, wherein one or more, or each, of the apertures include a valve that is movable between open and closed positions and is capable of regulating the uptake or inflow of gas; (ii) a first port for receiving the gas and comprising a first valve for regulating the flow of gas through the first port, said first valve being moveable between open and closed positions; and (iii) a second port for outputting gas, when contained in the chamber, and comprising a second valve for regulating the flow of gas through the second port, said valve being moveable between open and closed positions. Suitably, the chamber includes a base and comprises one more openings.

Suitably, the openings are threaded or non-threaded.

Suitably, the openings comprise a module in one or more of the openings.

Suitably, the module is threaded or non-threaded.

Suitably, the module is adapted for containing or storing a cell culture medium or for monitoring conditions in the chamber or for gas sampling or for gas characterisation Suitably, one or modules contain a cell culture medium.

Suitably, the cell culture medium comprises a culture of cells, suitably, a 2- or 3-dimensional culture of cells.

Suitably, the modules adapted for containing or storing a cell culture medium further comprise a microfluidic channel and optionally a microfluidic pump connected thereto.

Suitably, the module comprises quartz crystal microbalances.

Suitably, a connecting structure is joined to the second port.

Suitably, the connecting structure is hollow.

Suitably, the pump further comprises a motor.

Suitably, the pumping pressure of the pump corresponds to atmospheric pressure or above or below atmospheric pressure.

Suitably, the displacement volume of the pump is between about 0 and 100 ml or between about 1 and about 100 ml.

Suitably, the pump comprises stainless steel.

Suitably, the chamber is a cylinder.

Suitably, the chamber comprises glass.

Suitably, the chamber of the pump has a volume of about 100 ml.

In a further aspect there is provided a pump for displacing a volume of gas comprising: (i) a chamber configured for containing a volume of gas, said chamber comprising a base and one or more modules for containing or storing a cell culture medium or for monitoring conditions in the chamber or for gas sampling or for gas characterisation; and (ii) a port operable for receiving and outputting the gas.

Suitably, the pump is a piston pump.

Suitably, the modules are located in the base of the chamber.

Suitably, the modules are threaded or non-threaded.

Suitably, the modules are adapted to contain a cell culture medium or configured to store a cell culture medium or adapted to monitor conditions in the chamber or adapted to monitor conditions in the chamber or adapted to sample gas or adapted to characterise gas.

Suitably, the one or modules contain a cell culture medium.

Suitably, the cell culture medium comprises or is in contact with a culture of cells, suitably, a 2- or 3-dimensional culture of cells.

Suitably, the modules adapted for containing or storing a cell culture medium further comprise a microfluidic channel and optionally a microfluidic pump connected thereto.

Suitably, the module comprises quartz crystal microbalances.

Suitably, a connecting structure is joined to the port.

Suitably, the connecting structure is hollow.

Suitably, the pump further comprises a motor.

Suitably, the pumping pressure corresponds to atmospheric pressure or above or below atmospheric pressure.

Suitably, the displacement volume of the pump is between about 0 and 1000 ml or between about 1 and about 100 ml.

Suitably, the pump comprises stainless steel.

Suitably, the chamber is a cylinder.

Suitably, the chamber comprises glass.

Suitably, the volume of the chamber represents the volume of lung lumen or a part thereof.

In a further aspect, there is provided a connecting structure adapted for joining at least two pumps for transmitting a gas there between, said connecting structure comprising a hollow channel and or more threaded or non-threaded openings in the walls of the connecting structure.

Suitably, the threaded openings contain a threaded module in one or more of the openings, said module being adapted to contain a cell culture medium or configured to store a cell culture medium or adapted to monitor conditions in the chamber or adapted to monitor conditions in the chamber or adapted to sample gas or adapted to characterise gas.

Suitably, the one or modules contain a cell culture medium.

Suitably, the cell culture medium comprises or is in contact with a culture of cells, suitably, a 2- or 3-dimensional culture of cells.

Suitably, the modules adapted for containing or storing a cell culture medium further comprise a microfluidic channel and optionally a microfluidic pump connected thereto.

Suitably, the connecting structure is hollow.

Suitably, the connecting structure is branched.

Suitably, each terminating branch of the connecting structure is capable of being joined to a separate pump.

Suitably, the connecting structure represents the volume of conducting airways of the lung, suitably the human lung.

Suitably, the modules are positioned in a horizontal plane in the walls of the connecting structure.

Suitably, the modules are adapted to contain a culture of cells, suitably, a 2- or 3-dimensional culture of cells.

Suitably, the module is a chamber for containing a culture of cells, said chamber comprising a microfluidic channel and optionally a microfluidic pump connected thereto.

Suitably, the modules are adapted for monitoring conditions in the connecting structure and/or for gas sampling and/or for gas characterisation.

Suitably, the connecting structure comprises stainless steel.

There is also described a system comprising the pumps described herein.

Suitably, the system further comprises the connecting structure as described herein.

Suitably, the pumps are joined by the connecting structure.

In a further aspect, there is provided a method for simulating the interaction between a test atmosphere and a simulated respiratory tract comprising the use of the system described herein. There is also disclosed the use of the system as described herein for simulating the interaction between a test atmosphere and a simulated respiratory tract.

There is also disclosed a method for determining the effect of a test atmosphere on a culture of cells contained in a simulated respiratory tract comprising the use of the system described herein There is also disclosed the use of the system as described herein for determining the effect of a test atmosphere on a culture of cells contained in a simulated respiratory tract In a further aspect, there is disclosed a method for determining the effect of a test atmosphere on a culture of cells contained in a simulated respiratory tract comprising: (a) providing the system as described herein, wherein the system contains a culture of cells in one or more of the modules; and (b) comparing the culture of cells before and/or after exposure to the test atmosphere, wherein a difference between the culture of cells before and/or after exposure of the cells to the test atmosphere is indicative that the test atmosphere effects the culture of cells. A further aspect relates to a method for simulating the interaction between a test atmosphere and a simulated respiratory tract in the system described herein comprising: (a) with the first valve of the first pump open and the second valve of the first pump closed, providing a gas comprising a test atmosphere to the first pump via the first port; (b) closing the first valve and opening the second valve of the first pump and closing the valves on the piston plate of the first pump; (c) operating the second pump to draw the test atmosphere into the connecting structure and flushing the chamber of the first pump and the connecting structure with surrounding air; (d) opening the first valve of the first pump towards the surrounding air and forming a sealed connection between the first port and the second port of the first pump; and (e) after a period of time using the second pump to displace the test atmosphere through the connecting structure and through the first valve of the first pump.

There is further disclosed a method for determining the effect of a test atmosphere on a simulated respiratory tract in the system described herein comprising: (a) with the first valve of the first pump open and the second valve of the first pump closed, providing a gas comprising a test atmosphere to the first pump via the first port; (b) closing the first valve and opening the second valve of the first pump and closing the valves on the piston plate of the first pump; (c) operating the second pump to draw the test atmosphere through the connecting structure and flushing the chamber of the first pump and the connecting structure with surrounding air; (d) opening the first valve of the first pump towards the surrounding air and forming a sealed connection between the first port and the second port of the first pump; and (e) after a period of time using the second pump to displace the test atmosphere through the connecting structure and through the first valve of the first pump; wherein the test atmosphere contacts a cell culture located in one or more modules located in the first pump or the connecting structure or the second pump or a combination of two or more thereof and said method comprises the further step of determining the effect of the test atmosphere on the cell culture, wherein a difference in the cell culture before and/or after exposure to the test atmosphere is indicative that the test atmosphere effects the cell culture.

Suitably, the modules are adapted to monitor system conditions and/or for gas sampling and/or for gas characterisation and said method comprises taking one or more measurements from the modules.

There is also disclosed a method for simulating the interaction between a test atmosphere and a simulated respiratory tract comprising: (a) providing a test atmosphere to a chamber of a first pump; (b) withdrawing the test atmosphere from the first pump into a connecting structure that joins the first pump to a second pump; (c) flushing the first pump and at least of a portion of the connecting structure with surrounding air; (d) holding the test atmosphere in the second pump and the connecting structure for a defined period of time; (e) displacing the test atmosphere into the connecting structure and the first pump using the second pump; and (f) performing one or more pumping cycles of the surrounding air in the second pump; wherein the test atmosphere contacts a cell culture located in the first pump or the connecting structure or the second pump or a combination of two or more thereof.

Suitably, step (d) comprises holding the test atmosphere in the second pump and the portion of the connecting structure still containing test atmosphere for a defined period of time.

Suitably, the pumps are piston pumps comprising a piston plate and a base.

Suitably, the first pump is as defined in the embodiments of the present disclosure.

Suitably, the second pump is as defined in the embodiments of the present disclosure.

Suitably, the connecting structure is as defined in the embodiments of the present disclosure.

Suitably, the method is performed in a housing, suitably a temperature controlled housing.

Suitably, the temperature of the housing is controlled by a thermostat.

Suitably, the temperature in the housing is about 37° C.

Suitably, the different volumes of the first and second pumps represent the internal volume of different compartments of the respiratory tract, suitably, the human respiratory tract.

Suitably, the displacement volume of the first and second pumps is at least as large as the maximally achievable volume uptake in the corresponding compartment of the respiratory tract.

Suitably, the pumping pressure corresponds to atmospheric pressure or above or below atmospheric pressure.

Suitably, the displacement volume of the first pump is between about 0 and 100 ml or between about 1 and about 100 ml.

Suitably, the displacement volume of the second pump is between about 0 and 4000 ml or between about 1 and about 4000 ml.

Suitably, the chamber of the first pump has a smaller volume than the chamber of the second pump.

Suitably, the volume of the chamber of the first pump represents the volume of the oral and oropharyngeal cavity, suitably the human oral and oropharyngeal cavity.

Suitably, the volume of the chamber of the second pump represents the volume of lung lumen or a part thereof, suitably, the human lung lumen or a part thereof.

Suitably, the connecting structure represents the volume of conducting airways of the lung, suitably the human lung.

Suitably, the culture of cells is located on the base of the piston plate of the first and/or second pump and/or in the walls of the connecting structure.

Suitably, the culture of cells is a 2- or 3-dimensional culture.

Suitably, said method further comprises monitoring conditions and/or for gas sampling and/or for gas characterisation and in one or more of the first pump or the second pump or the connecting structure using one or more modules contained therein.

Suitably, the chamber comprising the culture of cells further comprises a microfluidic channel and optionally a microfluidic pump connected thereto.

Suitably, the connecting structure comprises stainless steel.

Suitably, the chamber of the first pump has a volume of about 100 ml.

Suitably, the chamber of the second pump has a volume of about 1 litre to about 4 litres.

In a further aspect there is described a method for determining the effect of a test atmosphere on a simulated respiratory tract comprising: (a) providing a test atmosphere to a chamber of a first pump; (b) withdrawing the test atmosphere from the first pump into a connecting structure that joins the first pump to a second pump; (c) flushing the first pump and at least of a portion of the connecting structure with surrounding air; (d) holding the test atmosphere in the second pump and the connecting structure for a defined period of time; (e) displacing the test atmosphere through the connecting structure and the first pump using the second pump; and (f) performing one or more pumping cycles of the surrounding air in the second pump; wherein the test atmosphere contacts a cell culture located in one or more modules located in the first pump or the connecting structure or the second pump or a combination of two or more thereof and said method comprises the further step of determining the effect of the test atmosphere on the cell culture, wherein a difference in the cell culture before and/or after exposure to the test atmosphere is indicative that the test atmosphere effects the cell culture.

Suitably, the modules are adapted to monitor system conditions and/or for gas sampling and/or for gas characterisation and said method comprises taking one or more measurements from the modules.

An apparatus configured to or adapted to perform the method(s) described herein is also disclosed.

SOME ADVANTAGES

Figure 1:
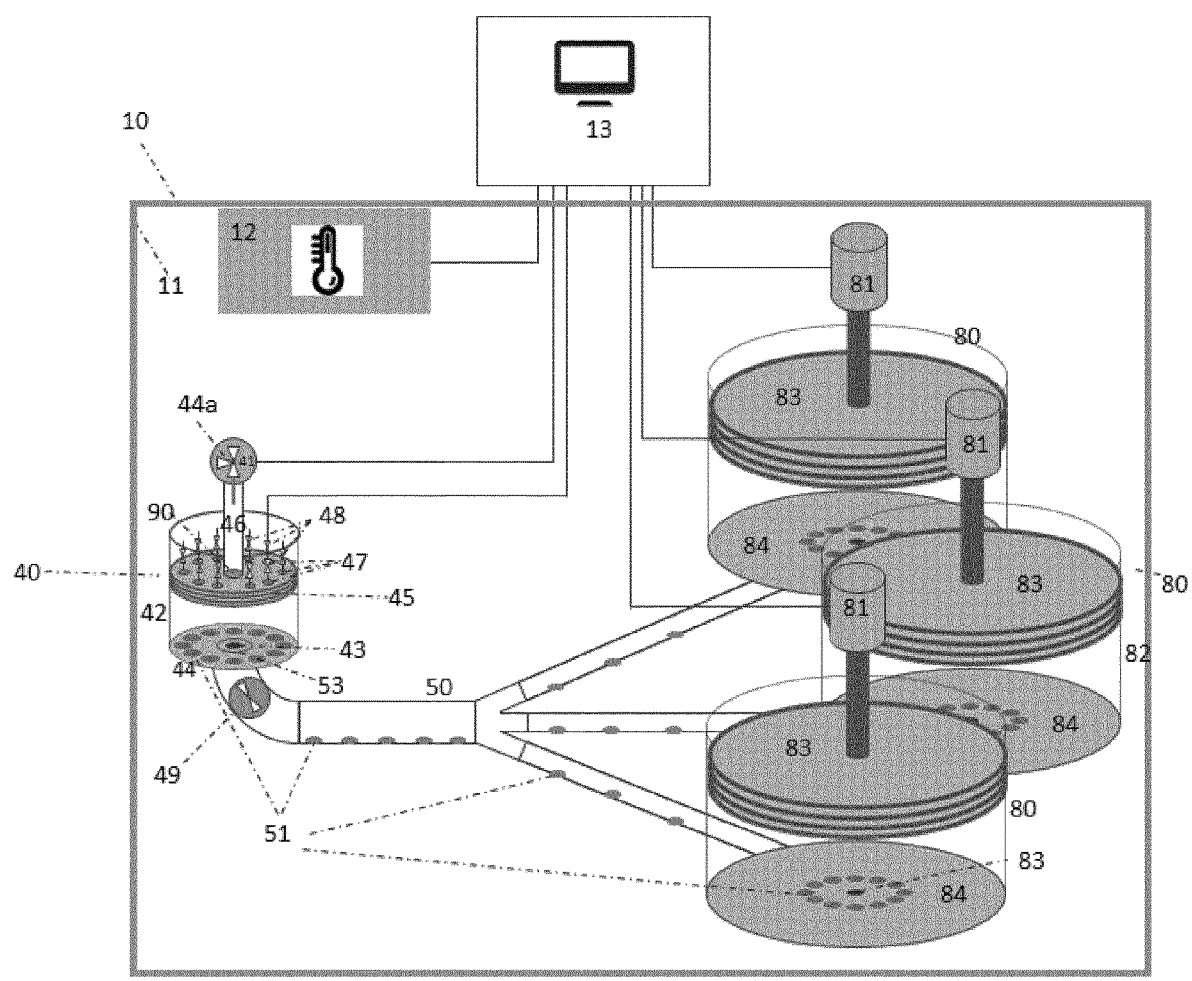
FIG. 1 is an illustration of a system 10 according to an embodiment of the present disclosure. The first pump 40 according to an embodiment of the present disclosure is also disclosed. The second pump 80 according to an embodiment of the present disclosure is also disclosed. The connecting structure 50 according to an embodiment of the present disclosure is also disclosed.

As the processes effecting the physicochemical properties of a test atmosphere in the respiratory tract as well as the mode of interaction between the two (for example, the dose delivery) are simulated by the system's physical and functional properties, clinically relevant dosing information may be obtained according to embodiments of the present disclosure.

The effects of one or more test atmospheres towards one or more compartments of the respiratory tract can be studied according to embodiments of the present disclosure.

The effects of one or more test atmospheres towards one or more compartments of the respiratory tract can be studied simultaneously or in stages, as required, according to embodiments of the present disclosure.

The modules that can be used in the system offer flexibility in relation to the exposed test system, the experimental endpoints and the exposure parameters to be monitored according to embodiments of the present disclosure.

The modules can be redesigned or changed according to specific requirements, without having to change the overall structure and function of the system according to embodiments of the present disclosure.

For many applications, the aerosol generation is driven by the system itself which means that aerosol generators/smoking machines are not required according to embodiments of the present disclosure. This can help to simplify the structure of the system.

In certain embodiments, the system can be modular in nature. This means that the various components—such as the pumps and the connecting structure, for example, can be exchanged individually and easily as required. Partial redesign, improvement or exchange of parts of the system according to specific requirements can be facilitated.

Mouth, breath-hold time and dynamic flow patterns occurring during breathing can be simulated according to embodiments of the present disclosure.

The present disclosure can, according to certain embodiments, account for a mouth hold-period during which highly dense aerosol can be allowed to age for up to several seconds prior to being pulled into the respiratory tract along with a large volume of dilution air.

DETAILED DESCRIPTION

The practice of the present disclosure employs, in certain embodiments, conventional techniques of engineering, microbiology, cell biology and biochemistry. The biological techniques are explained fully in the literature, such as, in Molecular Cloning: A Laboratory Manual, second edition (Sambrook et al., 1989) Cold Spring Harbor Press; Oligonucleotide Synthesis (M J. Gait, ed., 1984); Methods in Molecular Biology, Humana Press; Cell Biology: A Laboratory Notebook (J. E. CeIMs, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, I B. Griffiths, and D. G. Newell, eds., 1993-8) J. Wiley and Sons; Methods in Enzymology (Academic Press, Inc.); Current Protocols in Molecular Biology (F. M. Ausubel et al., eds., 1987); PCR: The Polymerase Chain Reaction, (Mullis et al., eds., 1994). Procedures employing commercially available kits and reagents will typically be used according to manufacturer-defined protocols unless otherwise indicated.

The technical terms and expressions used herein are generally to be given the meaning commonly applied to them in the pertinent art. All of the term definitions used herein apply to the complete content of this application.

The term "comprising" does not exclude other elements or steps.

The indefinite article "a" or "an" does not exclude a plurality.

The term "and/or" means, for example, (a) or (b) or both (a) and (b).

The terms "comprising", "comprises" and "comprised of" as used herein are synonymous with "including", "includes" or "containing", "contains", and are inclusive or open-ended and do not exclude additional, non-recited members, elements or method steps. The term "consisting of" means that additional components are excluded and has the recited elements only and no more.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosure. It is to be understood that the value to which the modifier "about" refers is itself also specifically, and preferably, disclosed.

Before discussing the embodiments in any more detail, first an overview will be provided. Embodiments provide apparatuses and methods that can be used in a variety of applications for studying the respiratory tract. For example, embodiments find utility in studying the deposition and/or condensation of one or more constituents present in a test atmosphere on internal surfaces of the apparatus, including their re-evaporation. Embodiments also provide for the evaluation of test atmospheres that can be investigated during their passage through the apparatus in order to study changes in aerosol concentration and/or aerosol particle growth and/or aerosol particle shrinkage. The effects of the test atmospheres towards biological test systems present inside the apparatus/system can be studied in embodiments of the present disclosure.

System

In one aspect, there is described a system 10 for determining the interaction between a test atmosphere and a simulated respiratory tract, said system comprising: (a) a first pump comprising: (i) a chamber configured for containing a first volume of gas comprising a test atmosphere; (ii) a first port adapted for receiving and outputting gas and comprising a valve for regulating the flow of gas through the first port, said valve being moveable between open and closed positions, wherein in the open position said valve is openable towards a test atmosphere or surrounding air; (iii) a second port adapted for outputting and receiving gas and comprising a valve for regulating the flow of gas through the second port, said valve being moveable between open and closed positions; and (iv) a motor for controlling the operation of the first pump; a second pump comprising: (i) a chamber configured for containing a second volume of gas, wherein the first and second volumes of gas are different; (ii) a port adapted for receiving and outputting gas; (iii) a piston plate in the chamber, said piston plate comprising one or more apertures for the uptake or inflow of gas into the chamber wherein one or more, or each, of the apertures include a valve that is movable between open and closed positions and is capable of regulating the uptake or inflow of gas; and (iv) a motor for controlling the operation of the second pump; (c) a connecting structure operable to transmit the gas from the first pump into the second pump; and (d) one or more openings in the first pump or the second pump or the walls of the connecting structure or a combination of two or more thereof, said openings being capable of receiving a module for containing or storing a cell culture medium or for monitoring conditions in the chamber or for gas sampling or for gas characterisation.

The gas can be a test atmosphere or it can comprise a test atmosphere.

FIG. 1 illustrates a system 10 according to an embodiment of the present disclosure. The system 10 includes at least two pumps 40, 80. The two or more pumps 40, 80 are connected to each other. In certain embodiments, the two or more pumps 40, 80 are connected to each other by a branched hollow structure 50. Each pump 40, 80 can be operated by its own individual motor 41, 81 or two or more pumps can be operated by the same motor 41, 81, as required. The complete system 10 can be located in a climatic housing 11 equipped with a thermostat 12 to control the temperature in the housing 11. The chambers of the pumps 40, 80 can be configured to represent the internal volumes of different compartments of a respiratory tract—such as a human or animal respiratory tract. They can be configured to provide a displacement volume at least as large as the maximally achievable volume uptake in the respective compartment of the respiratory tract. In particular, one (first) pump 40 can represent the volume of the oral and oropharyngeal cavity—such as a human or animal oral and oropharyngeal cavity. Another second pump 80 can represent the volume of the lung lumen or parts thereof—such as the lumen of individual lung lobes or smaller subunits, especially human or animal lung lumen or parts thereof. The branched hollow connecting structure 50 can represent the dimensions of the conducting airways—such as one or more of the nasopharyngeal cavity, hypopharynx, larynx, trachea, bronchi and bronchiolar structures down to the respiratory bronchioles, especially human or animal conducting airways. The branched hollow connecting structure 50 can represent the dimensions of the conducting airways—including the nasopharyngeal cavity, hypopharynx, larynx, trachea, bronchi and bronchiolar structures down to the respiratory bronchioles. The dimensions, for example, the diameters and lengths, as well as the branching pattern of the different sub-parts of the connecting structure 50 can resemble the tree of conducting airways.

As shown in FIG. 1, the branched hollow structure 50 can be connected to a central opening 43, 89 in the base 44, 84 of the chamber 42, 82 of each pump 40, 80. In certain embodiments, multiple openings, holes or sockets 51 can be present on the base 44, 84 of the chamber(s) 42, 82, which may be arranged symmetrically around the central opening 43, 89. Directly at the connection between the pump 40 and the connecting structure 50, a valve 44*a* can be used to allow sealing of the pump 40 from all other system parts.

The pump 40 representing the oral cavity can have one or more opening(s) 43 through which test atmosphere(s) and dilution air can leave the pump 40 towards the branched hollow structure 50. The point of entry and exit of a test atmosphere 90 is typically located on the piston plate 45 of the pump 40, suitably in the center thereof. It can run through a hollow piston axis 46, on top of which a valve 44*a*—such as a three way valve can be present. In embodiments, the valve 44*a* can be closed or opened towards a test atmosphere source or surrounding air. An array of one or more (for example, a plurality) apertures 47 through which surrounding air can enter the system is arranged on the piston plate 45, optionally in a radial arrangement. One or more valves 48 (for example, a plurality) on one or more, or all, of the apertures can be used to allow the opening or closing of one or more of these apertures 47. In certain embodiments, each aperture 47 is controlled by a valve 48. In certain embodiments, an array of one or more (for example, a plurality) apertures through which surrounding air can enter the system can be arranged on the piston plate 84 of the second pump, optionally in a radial arrangement. One or more valves (for example, a plurality) can be used to allow the opening or closing of one or more of these apertures. In certain embodiments, each aperture is controlled by a valve. In certain embodiments, an array of one or more (for example, a plurality) apertures through which surrounding air can enter the system can be arranged on the piston plate of the first and second pump, optionally in a radial arrangement. Advantageously, the branched hollow structure 50 can be disconnected from the pumps 40, 80. Advantageously, the branched hollow structure 50 can be disassembled to its primary parts. This can allow easy access for placing or removing test systems and/or for cleaning.

The bases 44, 84 of the pumps 40, 80 can be removed for placing/removing test systems and for cleaning.

In the base 44, 84 of each pump 40, 80 as well as in the different parts of the connecting structure 50, openings, holes or sockets 51—such as threaded or non-threaded openings, threaded or non-threaded holes or threaded or non-threaded sockets 113, 213—can be located therein. The openings, holes or sockets 51 can be located in various positions-such as on the bases 44, 84 of one or more of the pumps 40, 80, or they can be arranged around the central opening 43, 89 or in the branched hollow structure 50 at various locations of choice, suitably on the lower side of the branched hollow structure 50 or any combination thereof.

Figure 2:
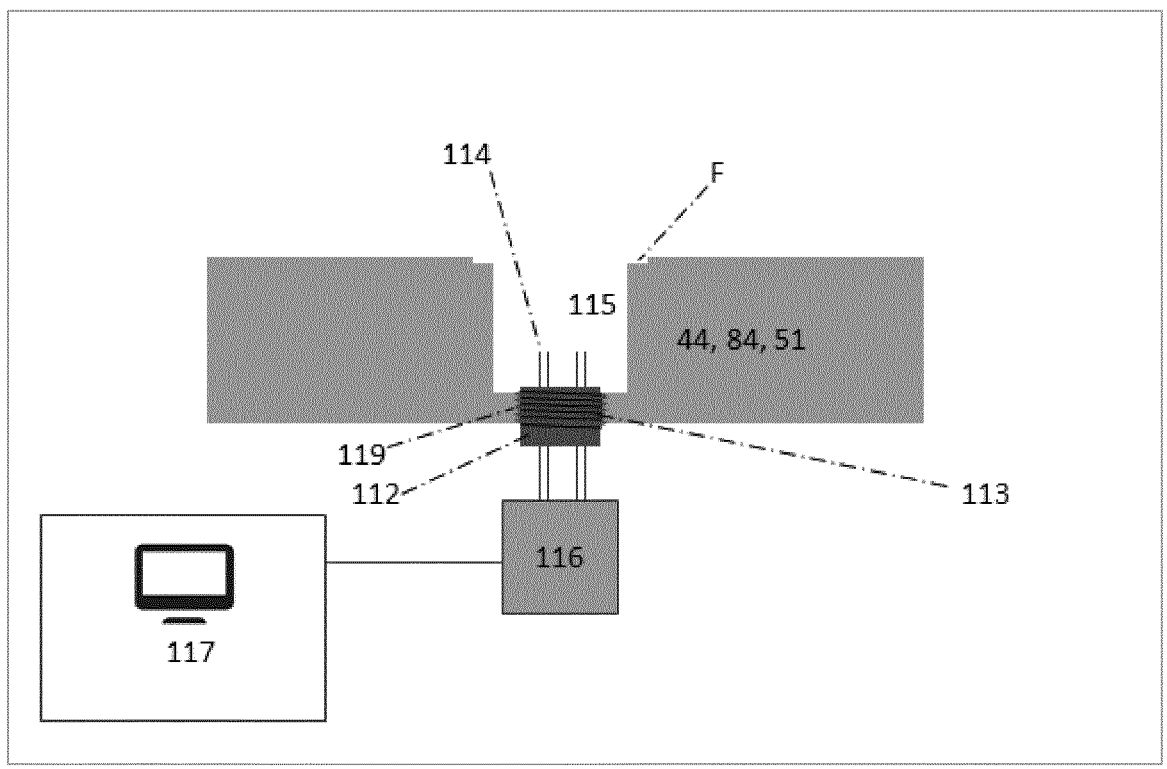
FIGS. 2 and 3 are illustrations of modules 113, 213 according to embodiments of the present disclosure.
Figure 3:
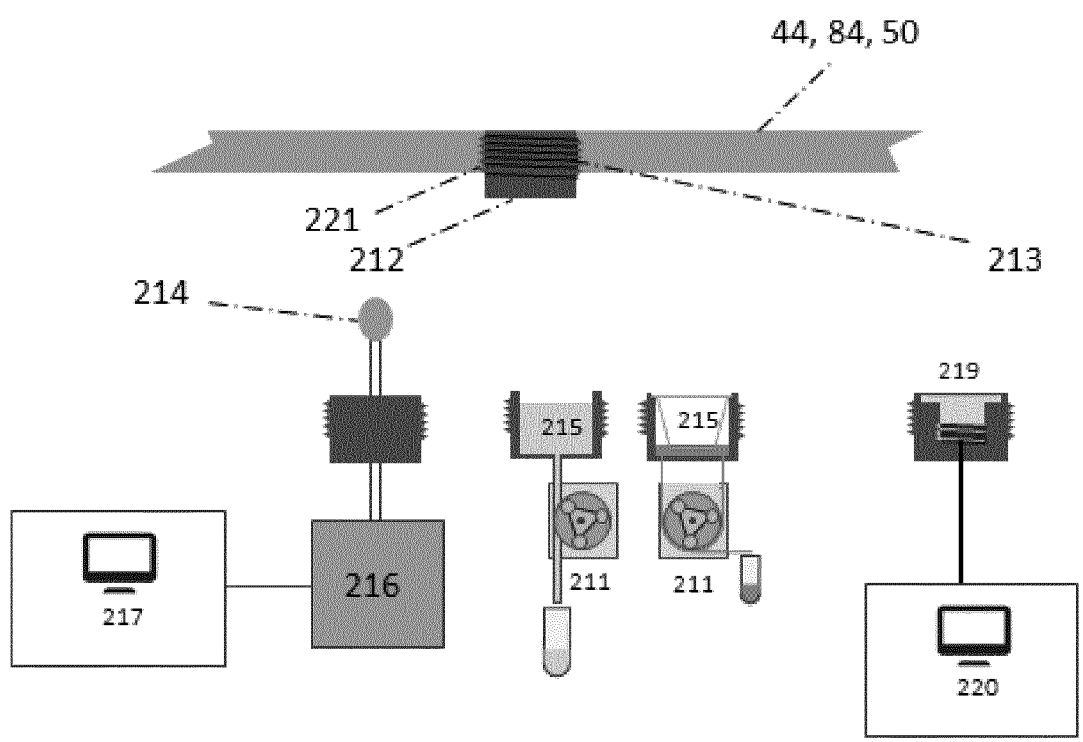

The openings, holes or sockets 51 can be used to allow mounting of various modules 112, 212 or devices therein or thereon which can be used to monitor the operation of the system 10 and/or to conduct experiments and/or to collect samples and the like. Examples of such modules 112, 212 or devices are shown in FIG. 2 and FIG. 3 and are described herein. Advantageously, the pumps 40, 80 that are used in the system 10 are therefore able to function not only to transport test atmospheres but they can also function as exposure chambers.

FIGS. 2 and 3 illustrate an embodiment of the disclosure in which the openings, holes or sockets 51 are in the optional form of threaded openings, holes or sockets 112, 212. The one or more openings, holes or sockets 51 can contain one or more modules 112, 212. The use of the thread facilitates the straightforward insertion and replacement of the module(s) 112, 212. The use of a thread in the openings, holes or sockets 51 is optional as the modules can be configured so they can be plugged or pushed into the openings, holes or sockets 51 in sealing engagement therewith. The modules can be a push-fit. Tightening can be achieved through the use of O-rings and the like.

The modules 112, 212 that are used can be adapted for various purposes depending on the requirements of the system being configured. For example, the modules 112, 212 can be adapted to contain or store a cell culture medium or for monitoring conditions in the chamber 42, 82 or for gas or liquid sampling or for gas characterisation and the like. The modules 112, 212 can be located on the base 44, 84 of the first 40 and/or second 80 pump and/or in the walls of the connecting structure 50. In a particular embodiment, the one or more modules 112, 212 can be configured to contain or store a cell culture medium. According to this embodiment, the one or more modules 112, 212 can be receptacles capable of holding a liquid or solution. The cell culture medium can comprise or it can be in contact with a culture of cells—such as a 2- or 3-dimensional culture of cells. In certain embodiments, the module(s) 113, 213 adapted for containing or storing a cell culture medium further comprise a microfluidic channel and optionally a microfluidic pump connected thereto. The modules 113, 213 will generally be positioned in a horizontal plane in one or more of the first pump 40 or the second pump 80 or the walls of the connecting structure 50.

As can be seen in FIGS. 2 and 3, the openings, holes or sockets 51 can optionally be configured to contain a threaded hole or socket 112, 212. The threaded hole or socket 113, 213 can comprise one or more probes 114, 214 of one or more devices 116, 216. Such devices 116, 216 can be used for monitoring internal system conditions or for test atmosphere characterization or for sampling and the like. The operation of the device(s) 116, 216 can be controlled by a computer 117, 217. The threaded hole or socket 113, 213 and/or the modules 112, 212 can be adapted for use as a cultivation chamber 115, 215 in which biological test systems (for example, organotypic cell cultures of the human respiratory tract epithelium as described herein), can be placed for test atmosphere exposure. The threaded openings, holes or sockets 113, 213 can be adapted for containing trapping agents in which the test atmosphere can be sampled for analyses. Sampling of the cell culture medium or trapping agent during test atmosphere exposure can be achieved by various means—including through the use of a microfluidic pump system 211. Modules 112, 212 holding quartz crystal microbalances (QCM, 219) can be used. The modules 112, 212 on which probes 214, chambers 215 or QCMs 219 can be mounted can be inserted into any chamber 42, 82 or interior of the branched hollow structure 50 of the system. The operation of the QCM(s) 219 can be controlled by a computer 220. The system 10 can be completely or partially controlled by a computer 13 as required. The system 10 can be partially or completely automated.

The system 10 can comprise one or more (for example, a plurality of) first pumps. The system 10 can comprise one or more (for example, a plurality of) second pumps. The system 10 can comprise one or more (for example, a plurality of) first pumps and one or more second pumps.

First Pump

In one aspect, there is disclosed a pump—suitably a piston pump—for displacing a volume of gas comprising: (i) a chamber configured for containing a volume of gas and comprising a base and one or more openings capable of receiving a module for containing or storing a cell culture medium or for monitoring conditions in the chamber or for gas sampling or for gas characterisation; (ii) a first port for receiving and outputting the gas, when contained in the chamber, and comprising a first valve for regulating the flow of gas through the first port, said first valve being moveable between open and closed positions, wherein in the open position said valve can be opened towards a test atmosphere or surrounding air; (iii) a second port for outputting and receiving gas, when contained in the chamber, and comprising a second valve for regulating the flow of gas through the second port, said valve being moveable between open and closed positions; and (iv) a piston plate in the chamber, said piston plate comprising one or more apertures for the uptake or inflow of gas into the chamber wherein one or more, or each, of the apertures include a valve that is movable between open and closed positions and is capable of regulating the uptake or inflow of gas.

There is also disclosed a piston pump for displacing a volume of gas comprising: (i) a chamber configured for containing a volume of gas and containing a piston plate comprising one or more apertures for the uptake or inflow of gas into the chamber, wherein one or more, or each, of the apertures include a valve that is movable between open and closed positions and is capable of regulating the uptake or inflow of gas; (ii) a first port for receiving the gas and comprising a first valve for regulating the flow of gas through the first port, said first valve being moveable between open and closed positions; and (iii) a second port for outputting gas, when contained in the chamber, and comprising a second valve for regulating the flow of gas through the second port, said valve being moveable between open and closed positions.

As shown in FIG. 1, the system 10 can contain the first pump 40 for displacing a volume of gas. The first pump 40 is disclosed herein as a separate aspect of the present disclosure and its use is not limited to use in the system 10 described herein.

The first pump can be a primary pump, so called due to its location in the system as the entry point for a gas. It comprises a chamber 42 (for example, a cylinder) configured for containing a volume of gas and comprises a base 44 and one or more openings 43 capable of receiving a module—such as a threaded or non-threaded module 113, 213 in a hole or socket 112, 212 as shown in FIGS. 2 and 3 and as described herein. It also contains a first port 90 for receiving and outputting gas, when contained in the chamber 42, and comprises a first valve 44a—such as a three way valve for regulating the flow of gas through the first port 90, said first valve 44a being moveable between open and closed positions, wherein in the open position the valve 44a can be opened towards a test atmosphere or surrounding air. It also contains a second port 43 for outputting and receiving gas, when contained in the chamber 42. Suitably, the second port 43 is configured as an opening. At the connection between the first pump 40 and the connecting structure 50, a second valve 49 at the location of the second port 43 allows sealing of the pump 40 from other system parts. The second valve 49 can be used for regulating the flow of gas through the second port 43, said second valve 49 being moveable between open and closed positions. As can be seen in FIG. 1, the pump 40 can be a piston pump comprising a piston plate 45. One or more of the openings, holes or sockets 51 in the chamber 42 can be threaded 112, 212 or non-threaded. One or more of the openings, holes or sockets 51 in the chamber 42 can comprise a module 113, 213—such as a threaded or non-threaded module 113, 213, as discussed herein. The pump 40 further comprises a motor 41 to control the operation of the pump. The pumping pressure of the motor 41 can correspond to atmospheric pressure or it can be above or below atmospheric pressure as required. In certain embodiments, the pumping pressure of the motor 41 can be above or below atmospheric pressure to displace a test atmosphere. The displacement volume of the pump 40 can be between about 0 and 100 ml or between about 1 and about 100 ml. The chamber 42 of the pump 40 can have a volume of up to about 100 ml. The pump 40 can be manufactured from various materials that are known in the art—such as stainless steel. Suitably, the chamber 42 is a cylinder. Suitably, the chamber 42 can be made of glass. The piston plate 45 of the pump 40 comprises one or more apertures 47 for the uptake or inflow of gas. The one or more of the apertures 47 can include a valve 48 that is movable between open and closed positions and is capable of regulating the uptake or inflow of gas.

As also shown in FIG. 1, the pump 40 can be a piston pump for displacing a volume of gas. The piston pump comprises a chamber 42 (for example, a cylinder—such as a glass cylinder) configured for containing a volume of gas and containing a piston plate 45 comprising one or more apertures 47 for the uptake or inflow of gas into the chamber 42. One or more of the apertures 47 or each of the apertures 47 comprise a valve 48 for regulating the uptake or inflow of gas through the apertures 47.

It can include a first port 90 for receiving the gas and a first valve 44a—such as a three way valve—for regulating the flow of gas through the first port 90. The first valve 44a is moveable between open and closed positions. It also includes a second port 43 for outputting gas, when contained in the chamber 42, the second port 43 optionally comprising a second valve for regulating the flow of gas through the second port 43, the valve being moveable between open and closed positions. The chamber 42 can include a base 44a and one more openings 43. The base can additionally include one or more openings, holes or sockets 51 which can be threaded 119 or non-threaded and/or they may comprise a module 113, 213, as discussed herein. A connecting structure 50—such as a hollow connecting structure—can be joined to the second port 43. The pump 40 can further comprise a motor 41 in which the pumping pressure corresponds to atmospheric pressure or above or below atmospheric pressure. The displacement volume of the pump 40 can be between about 0 and 100 ml or between about 1 and about 100 ml. The chamber 42 of the pump 40 can have a volume of about 100 ml.

A system comprising two or more first pumps is contemplated. The use of the two or more first pumps in a system for determining the interaction between a test atmosphere and a simulated respiratory tract is also contemplated.

A method for culturing a cell in the first pump is also contemplated. The use of the first pump for culturing a cell is also disclosed.

Second Pump

In a further aspect, there is disclosed a pump for displacing a volume of gas comprising: (i) a chamber configured for containing a volume of gas, said chamber comprising a base and one or more modules for containing or storing a cell culture medium or for monitoring conditions in the chamber or for gas sampling or for gas characterisation; and (ii) a port operable for receiving and outputting the gas. As shown in FIG. 1, the system can contain a second pump 80 for displacing a volume of gas comprising a chamber 82—such as a cylinder—configured for containing a volume of gas, said chamber 82 comprising a base 84 and one or more modules 113, 213 for containing or storing a cell culture medium or for monitoring conditions in the chamber 82 or for gas sampling or for gas characterisation and the like. The second pump can be a secondary pump.

The second pump 80 is disclosed herein as a separate aspect of the present disclosure and its use is not limited to use in the system 10 described herein.

The second pump 80 further includes a port 89 operable for receiving and outputting the gas. As shown in FIG. 1, the second pump 80 can be a piston pump comprising a piston plate 83. The piston plate 83 can be free of any apertures or openings. The modules 113, 213—such as threaded or non-threaded modules 113, 213, as discussed herein-can be located in the base 84 of the chamber 82. A connecting structure 50—such as a hollow connecting structure-can be joined to the port 89. The second pump 80 further comprises a motor 81. The pumping pressure of the second pump 80 will generally correspond to atmospheric pressure or above or below atmospheric pressure. The displacement volume of the pump can be between about 0 and about 1000 ml or between about 0 and about 4000 ml or between about 1 and about 1000 ml or between about 1 and about 4000 ml. The volume of the chamber 82 can represent the volume of lung lumen or a part thereof. In certain embodiments, an array of one or more (for example, a plurality of) apertures through which surrounding air can enter the system can be arranged on the piston plate 84, optionally in a radial arrangement. One or more valves (for example, a plurality) can be used to allow the opening or closing of one or more of these apertures. In certain embodiments, each aperture is controlled by a valve.

A system comprising two or more second pumps is contemplated. The use of the two or more second pumps in a system for determining the interaction between a test atmosphere and a simulated respiratory tract is also contemplated.

A method for culturing a cell in the second pump is also contemplated. The use of the second pump for culturing a cell is also disclosed.

Connecting Structure

A connecting structure operable to transmit or carry a gas between two or more pumps is also disclosed. The connecting structure can be a tube or a pipe or a conduit or the like through which a gas can be conducted or conveyed. The connecting structure can be adapted for connecting at least two pumps for transmitting or carrying a gas there between. The connecting structure can join a first pump at the second port of the first pump described herein and the port of the second pump described herein. The connecting structure can comprise a hollow channel and one or more openings—such as threaded or non-threaded openings—in the walls of the connecting structure. The connecting structure can be used in the systems and methods described herein. The system can comprise a connecting structure adapted for joining at least two pumps for transmitting a gas there between.

An embodiment of the connecting structure 50 is shown in FIG. 1. The connecting structure will generally comprise a hollow channel. It will generally be branched. In embodiments, each terminating branch of the connecting structure can be joined to separate pumps 40, 80 when it is contained in a system. The connecting structure 50 can comprise one or more openings—especially threaded or non-threaded openings—in the walls of the connecting structure. The threaded or non-threaded openings can contain a module 112, 212. The module 112, 212 can be adapted for containing a culture medium and/or monitoring system conditions and/or for gas sampling and/or for gas characterisation, as discussed herein. The connecting structure can, in certain embodiments, be branched with two or more branches. Each terminating branch of the connecting structure can be joined to a separate pump. The connecting structure can represent the volume of conducting airways of the lung. The connecting structure 50 can be made of various materials. In certain embodiments, the use of stainless steel is preferred.

A method for culturing a cell comprising the connecting structure is also contemplated. The use of the connecting structure for culturing a cell is also disclosed.

System Operation and Function

The system can be completely or partially controlled by a computer, as required. This can allow synchronized operation of some or all of the pumps and valves. This can allow synchronized operation of some or all of the elements of the system. The computer can be used to set the stroke length of one or more of the pumps and/or the stroke speed of one or more of the pumps. The computer can be used to control the temperature of the system.

The operation of an embodiment of the system 10 as depicted in FIG. 1 will now be described. In resting state, the piston of the first pump 40 is in a down stroke position, the position of the second pump 80 is in a position for retaining a defined volume of gas in the chamber 82 and the valves 48, 49 are closed. A test atmosphere is taken up into the pump 40 which can represent the oral cavity. This inflow can be driven by the pump 40 and can enter the chamber 42 via the hollow piston axis 46. The hollow piston axis 46 can be directly connected to the test atmosphere source. Once the pump 40 has completed the upstroke, the valve 44*a*, which can be a three-way valve, at the central opening on top of the hollow piston axis 46 closes, and the valves 48 regulating the inflow of surrounding air through apertures 47 in the piston plate 45 and the valve 49 at the inlet to the connecting structure 50 open.

The test atmosphere is withdrawn from the chamber 42 which can represent the oral cavity through the connecting structure 50 which can represent the conductive airways. This can be driven by the upstroke of the second pump 80 which can represent the lung lumen or parts thereof. As the total displacement volume of the second pump 80 can be a multiple of the volume of the pump 40, the chamber 42 of the pump 40 as well as at least parts of the connecting structure 50 can be flushed with surrounding air which can enter the first pump 40 through the apertures 47 in the piston plate 45.

At the first pump 40, the valve 44*a* on top of the piston axis 46 can open towards the surroundings. The valves 48 on the piston plate 45 can close and the pump 40 performs a down stroke. In its down stroke position, this pump 40 can form a sealed connection between the hollow piston axis 46 and the opening 43 in the base 44. The sealed connection can be achieved by means of a gasket 53. The gasket 53 can be located either on the base 44 or the piston plate 45. After a defined 'breath holding time', the second pump 80 can then perform a down stroke, thereby displacing the test atmosphere through the connecting structure 50 and through the piston axis 46 of the first pump 40, directly to the surroundings. With the pump 40 remaining in its down stroke position and the valve 44*a* remaining opened towards the surroundings, the second pump(s) 80 can perform one or more (for example, several) cycles of breathing surrounding air before the valve 44*a* opens again towards the test atmosphere source and the next cycle of test atmosphere inhalation starts.

In a further aspect, there is provided a method of comprising: (a) providing a pump—such as the first pump described herein—comprising a chamber; (b) withdrawing a gas—such as a test atmosphere—from the pump into a connecting structure that joins the pump to a further pump—such as the second pump described herein; (c) flushing the pump provided in step (a) and at least of a portion of the connecting structure with surrounding air; (d) holding the gas in the further pump and the connecting structure for a defined period of time; (e) displacing the gas into the connecting structure and the pump provided in step (a) using the further pump; and (f) performing one or more pumping cycles of the surrounding air in the further pump.

In a further aspect, there is provided a method comprising: (a) providing a gas—such as a test atmosphere—to a chamber of a pump—such as the first pump described herein; (b) withdrawing the gas from the pump described in step (a) into a connecting structure that joins the pump to a further pump—such as the second pump described herein; (c) flushing of the pump of step (a) and at least of a portion of the connecting structure with surrounding air; (d) holding the gas in the further pump and the connecting structure for a defined period of time; (e) displacing the gas through the connecting structure and the pump of step (a) using the further pump; and (f) performing one or more pumping cycles of the surrounding air in the further pump.

Test Atmosphere Generation

Test atmospheres—such as aerosols—to be studied using the disclosed system 10 and methods can be generated via various means. For many applications, for example, for testing tobacco products or common medical inhalers and the like, the test atmosphere generation can be driven by the system itself, that is, the primary or secondary pumps themselves generate the negative pressure required for generation and extraction of the test aerosol, which means that the use of aerosol generators/smoking machines is advantageously not required.

The test atmosphere can be an environmental sample of gases or aerosols, for instance for monitoring room air quality, occupational exposures or environmental pollution in close proximity to industrial sites. In this particular case, the test atmosphere is not generated, but sampled by the action of the system.

The test atmosphere can be an aerosol—such as smoke or it can be derived from smoke. As used herein, the term 'smoke' is used to describe a type of aerosol that is produced by smoking articles, such as cigarettes, or by combusting an aerosol forming material. Smoke includes various agents, which can be provided as individual compounds for study if required. Examples of such agents include nicotine-free dry particulate matter, carbon monoxide, formaldehyde, acetaldehyde, acetone, acrolein, propionaldehyde, crotonaldehyde, methyl-ethly ketone, butyraldehyde, benzo[a]pyrene, phenol, m-cresol, o-cresol, p-cresol, catechol, resorcinol, hydroquinone, 1,3-butadiene, isoprene, acrylonitrile, benzene, toluene, pyridine, quinoline, styrene, N'-nitrosornicotine (NNN), N'-nitrosoanatabine (NAT), N'-nitrosoanabasine (NAB), 4-(methylnitrosamino)-1-(3-pyridyl)-1-butanone (NNK), 1-aminonaphthalene, 2-aminonaphthalene, 3-aminobiphenyl, 4-aminobiphenyl, nitrogen monoxide (NO), nitrous oxide (NOx), cyanhydric acid, ammonia, arsenic, cadmium, chrome, lead, nickel, selenium and mercury.

When the aerosol is smoke, the system 10 can optionally be connected to a smoking machine Suitably, the smoking machine holds and lights cigarettes with the pumps being provided by the system or pumps of the present disclosure. A defined number of puffs per cigarette and a defined number of puffs per minute of exposure can be used and the number of cigarettes varied to adjust to the exposure times. Reference cigarettes—such as the reference cigarettes 3R4F—can be used as the source of the smoke and smoked on the smoking machine in basic conformity with the International Organization for Standardization smoking regimen (ISO 2000).

The use of a control atmosphere is also contemplated—such as an atmosphere that does not contain the test atmosphere. The use of the control atmosphere can help to determine the effect of the test atmosphere in comparison to the control atmosphere.

The system 10 can be connected to a smoking machine by means of a suitable conduit, which provides a flow path for the smoke to the system 10. The smoke may be transferred through the conduit with or without a carrier gas, such as air. Where a carrier gas is used, the conduit preferably comprises an inlet for the introduction of the carrier gas into the conduit, to mix with the smoke stream. The conduit can comprise at least one inlet for the introduction or injection of a standard reference into the system 10)—such as nicotine—for the purposes of calibration. The smoke flow will generally be controlled by the system or pumps of the present disclosure.

The smoking machine may be a linear or rotary smoking machine. Suitably, the smoking machine is operated to smoke a plurality of smoking articles simultaneously such that the cumulative smoke from the plurality of smoking articles can be collected and analysed. Suitable smoking machines for use in the present disclosure are well known to the skilled person.

The system 10 and method described herein can be used to perform an analysis of the mainstream smoke generated by a smoking article during the smoking test. The 'mainstream smoke' refers to the smoke that is drawn through the smoking article and which would be inhaled by the consumer during use.

The test atmosphere may be from an 'aerosol-generating device', which is a device that interacts with an aerosol-forming substrate to generate an aerosol. An example of an aerosol is smoke. The aerosol-forming substrate may be part of an aerosol-generating article. An aerosol-generating device may comprise one or more components suitable for generating an aerosol from an aerosol generating substrate. An aerosol-generating device may be an electrically heated aerosol-generating device, which is an aerosol-generating device comprising a heater that is operated by electrical power to heat an aerosol-forming substrate of an aerosol-generating article to generate an aerosol. The aerosol-generating device may be a gas-heated aerosol-generating device, a device heated by a carbonaceous heat source, other exothermal chemical reaction, or a heat sink. Other suitable means to generate an aerosol are well known in the art. An aerosol-generating device may be a device that interacts with an aerosol-forming substrate of an aerosol-generating article to generate an aerosol that is directly inhalable into a user's lungs thorough the user's mouth.

Another example of an 'aerosol-generating device' is an inhalation device (inhaler) which is generally used to deliver an aerosol containing an active ingredient—such as a medically active compound. Such inhalation devices are generally used for the delivery of aerosolised medicaments to the respiratory tract. They can be used for the treatment of respiratory and other diseases. Such inhalers are well known in the art and are generally of the pressurised metered type, the dry powder type or the nebulizer type. Generally, the medicament is in the form of a pressurized formulation containing fine particles of one or more medicinal compounds suspended in a liquefied propellant, or a solution of one or more compounds dissolved in a propellant/co-solvent system. Such formulations are well known in the art.

As used herein, the term 'aerosol-forming substrate' relates to a substrate capable of releasing volatile compounds that can form an aerosol. Such volatile compounds may be released by heating the aerosol-forming substrate. An aerosol-forming substrate may be adsorbed, coated, impregnated or otherwise loaded onto a carrier or support. An aerosol-forming substrate may conveniently be part of an aerosol-generating article or smoking article. In certain applications, the aerosol-forming substrate is contained in an aerosol-generating article, for example a rod-shaped aerosol-generating article such as a heated aerosol-generating article or heated cigarette. The aerosol-generating article is of suitable size and shape to engage with the aerosol-generating device so as to bring the aerosol-forming substrate into contact with the heater.

An aerosol-forming substrate may comprise medically active compounds or medicaments—such as antibiotics or anti-inflammatory agents that can be delivered to a patient via the respiratory tract. Numerous medical inhalation devices (inhalers) are known and routinely prescribed for treating various respiratory tract related and non-respiratory tract related diseases.

An aerosol-forming substrate may comprise nicotine. An aerosol-forming substrate may comprise tobacco. The aerosol-forming substrate may comprise, for example, a tobacco-containing material containing volatile tobacco flavor compounds, which are released from the aerosol-forming substrate upon heating. In certain embodiments, an aerosol-forming substrate may comprise homogenised tobacco material, for example cast leaf tobacco. As used herein, "homogenised tobacco material" refers to material formed by agglomerating particulate tobacco. Homogenised tobacco may be in the form of a sheet. Homogenised tobacco material may have an aerosol-former content of greater than 5% on a dry weight basis. Homogenised tobacco material may alternatively have an aerosol former content of between 5% and 30% by weight on a dry weight basis. Sheets of homogenised tobacco material may be formed by agglomerating particulate tobacco obtained by grinding or otherwise comminuting one or both of tobacco leaf lamina and tobacco leaf stems. Alternatively, or in addition, sheets of homogenised tobacco material may comprise one or more of tobacco dust, tobacco fines and other particulate tobacco byproducts formed during, for example, the treating, handling and shipping of tobacco. Sheets of homogenised tobacco material may comprise one or more intrinsic binders, that is tobacco endogenous binders, one or more extrinsic binders, that is tobacco exogenous binders, or a combination thereof to help agglomerate the particulate tobacco; alternatively, or in addition, sheets of homogenised tobacco material may comprise other additives including, but not limited to, tobacco and non-tobacco fibers, aerosol-formers, humectants, plasticisers, flavourants, fillers, aqueous and non-aqueous solvents and combinations thereof.

Cell Cultures

Cell cultures for use in the present disclosure include 2-dimensional and 3-dimensional cell cultures. As described herein, the cell culture will, in general, be contained or cultured in the one or more modules of the one or more pumps and/or the connecting structure. The cell culture can be exposed to a test atmosphere such that the effect of the test atmosphere on the cell culture can be determined. Suitably, two or more cell cultures will be located at different positions around the one or more pumps and/or the connecting structure and/or the system so that the effect of the test atmosphere on the cell cultures at these different locations—which mimic the respiratory tract—can be determined. 2-dimensional cell cultures involves growing cells in flat layers on plastic surfaces which permits the study of several aspects of cellular physiology and responses to stimuli—such as test atmosphere(s), but they do not reflect the real structure and architecture of an organ. In 2-dimensional monolayers, the extracellular matrix, the cell-to-cell and cell-to-matrix interactions, which are essential for the differentiation, proliferation and cellular functions are lost. 3-dimensional culture systems can form a functional tissue with similar features to those observed in vivo. As compared to the 2-dimensional culture systems, 3-dimensional cell culture allows cells to interact with their surroundings in all three dimensions and are more physiologically relevant. Such cells can show improvements in viability, proliferation, differentiation, morphology, response to stimuli, drug metabolism, gene expression and protein synthesis and the like. 3-dimensional cell culture can produce specific tissue-like structures and mimic functions and responses of real tissues in a manner that is more physiologically relevant than traditional 2-dimensional cell monolayers. Several 3-dimensional tissues mimicking human organs are commercially available. Lung 3-dimensional organotypic tissues, which are of specific interest in the context of the present disclosure can be prepared using primary human cells grown at an air-liquid interface (ALI) where these cells will differentiate and form a functional tissue. These 3-dimensional tissues bear close morphological resemblance and metabolic characteristics to human bronchial tissues. They are composed of basal, goblet and ciliated cells arranged in a pseudostratified structure. Similar to the lung, actively beating cilia are present allowing the study of their function and activity. Similar levels of xenobiotic enzyme-encoding mRNA have been found in these 3-dimensional ALI cultures compared with human lungs. In addition, these tissues can be maintained in vitro for an extended period of time. This 3-dimensional model of lung tissue is an appropriate model to explore the effects of test atmospheres and the like in accordance with the present disclosure. The term "3-dimensional cell culture" includes any method that provides for the culture of a cell in 3 dimensions, with or without the use of a matrix or scaffold. A number of different 3-dimensional cell culture methods have been developed including, spheroid cultures and organotypic cultures.

Spheroids

The term "spheroid" assumes the meaning as normally understood in the art which is either a single cell that divides into a ball of cells in 3-dimensions, or an aggregation of multiple cells in 3-dimensions, either with or without the use of a matrix or scaffold to support in 3-dimensional cell growth within the spheroid. The 3-dimensional spheroid can be an adherent spheroid or a spheroid grown in suspension. Several different systems for culturing spheroids for use in the present disclosure are available, including spheroids grown as aggregates, for example, on nanoculture plates, in suspension culture, on gels, on plastic coated with poly-HEMA, via cell encapsulation or as aggregates via a hanging droplet system. Other methods include the use of spinner flasks, rotation systems, concave plate methods and liquid-overlay. Bioreactors can also be adapted for use in 3-dimensional spheroid cell culture. In one embodiment, the method used is the hanging droplet system—such as the Gravity-PLUS Hanging Drop System (InSphero). This method involves the use of the GravityTRAP ULA Plate which is a non-adhesive coated microtiter plate designed for the production of spheroids. Spheroid maturation typically occurs within 2 to 5 days of seeding depending on the cell type and culture conditions. Suitably, the spheroids are cultured in a volume of 100 μl or more, or 200 μl more, or 300 μl or more. Suitably, the spheroids are cultured in Corning® spheroid microplates.

3-dimensional cell culture matrices or scaffolds can be used for spheroid culture. These are often porous substrates that can support 3-dimensional cell growth and differentiation. A variety of materials have been developed to produce 3-dimensional scaffolds with differences in physical appearance, porosity, permeability, mechanical characteristics, and nano-scale surface morphology. Examples of such materials include: collagen gels, sponges or biogels; fibrin; fibronectin; laminin; alginates, hydrogels; cross-linked glycosaminoglyca; polymer-based scaffold, synthetic scaffolds; peptide scaffolds; and chitosan composite scaffolds.

3-dimensional spheroids more closely resemble in vivo tissue in terms of their cellular communication and development of extracellular matrices. These matrices assist the cells in moving within the spheroid similar to the way cells would move in living tissue. The spheroids are thus much improved models for differentiation, survival, cell migration, cell polarisation, gene expression and growth.

Spheroids can be harvested and studied using various methods well known in the art, including colorimetric, fluorescence, and luminescence assays measured with a plate reader or they can be readily observed by microscopy. Additional techniques include western, northern or southern blot, histological techniques (for example, immunohistrochemistry, in situ hybridization, immunoflourescence) and the like. The use of optical imaging methods—such as inverse bright field microscopy, fluorescence microscopy, single-photon emission computed tomography (SPECT), positron emission topography (PET), magnetic resonance imaging (MRI) and Cerenkov luminescence imaging (CLI) techniques is also contemplated.

Applications of the use of 3-dimensional spheroids include the study of the proliferation of cells and tissues in vitro in an environment that more closely approximates that found in vivo, the screening of compounds and test atmospheres, toxicology assays and clinical trials and the like. The use of spheroids in 3-dimensional cell culture is generally reviewed in *Expert Opin. Drug Discov.* (2015) 10, 519-540. In vitro, lung spheroid cells can be expanded in large quantity and can form alveoli-like structures and acquire mature lung epithelial phenotypes.

Cell Sources

Lung cells and cell lines for use in the present disclosure can be isolated from a tissue or a fluid using methods that are well known in the art. They can be differentiated from stem cells—such as embryonic stem cells or induced pluripotent stem cells, or directly differentiated from somatic cells. Cells and cell lines may be or may be derived from human or animal subjects or from human or animal cells, including any of a number of mammalian species, suitably human, but including rat, mouse, pig, rabbit, and non-human primates and the like. Cells and cell lines can be obtained from commercial sources. In certain embodiments, the use of human cells is desirable.

Lung cells—including lung epithelial cells—are a cell type of interest. Bronchial and/or airway epithelial cells are of particular use in the present disclosure. Human bronchial epithelial cells can be collected by brushing donor lungs during a bronchoscopy procedure. In one embodiment, the lung cells are Normal Human Bronchial Epithelial (NHBE) cells. The lung epithelial cells can be cultured as a monolayer of undifferentiated cells or further developed into an organotypic lung epithelium-like tissue at an air-liquid interface. Cells can be established at an air-liquid interface using the following methodology. Briefly, epithelial cells can be cultured in a flask to increase the number of cells. After a period of incubation, cells are detached from the flask, counted and seeded onto inserts. On these inserts, cells are incubated with medium on the apical and basal sides. This phase ensure that the cells will divide and completely cover the insert to form an epithelium. Then, apical medium is removed, the basal medium is retained and replaced with a more complete medium. Cultures are incubated like this for a further period of time. In the meantime, the cells will differentiate into 3 cell types: basal, goblet and ciliated cells. At the end of the maturation, the cultures are ready to use. The use of the air liquid interface to culture human nasal epithelial cells is described in *J Vis Exp*. 2013; (80): 50646.

Lung epithelial cells can be obtained from human or animal subjects with different pathologies, including subjects that are classified as smokers or non-smokers.

Assays

The present disclosure can be used for a variety of applications for studying the impact of a test atmosphere(s) on a simulated respiratory tract. For example, the present disclosure can be used in the study of in vitro inhalation toxicology, the investigation of aerosol dynamics in the respiratory tract (for example, aerosol particle deposition and absorption of gases into cell cultures) or investigation of metabolic activity or transport of a test atmosphere(s) (for example, aerosol molecules) across the epithelia of the respiratory tract. The present disclosure can be used for testing the effect of aerosol(s), smoke or tobacco products or the effect of inhalers—such as medical inhalers. The present disclosure can be used for testing the effect of aerosol(s), smoke or tobacco products or the effect of medical inhalers on cells of one or more parts of the respiratory tract.

One aspect relates to a method for determining the effect of a test atmosphere on a culture of cells—such as one or more cultures of cells—contained in a simulated respiratory tract comprising: (a) providing the system described herein, wherein the system contains a culture of cells in one or more of the modules; and (b) comparing the culture of cells before and/or after exposure to the test atmosphere, wherein a difference between the culture of cells before and/or after exposure of the cells to the test atmosphere is indicative that the test atmosphere effects the culture of cells.

In the embodiment where a difference between the culture of cells is determined after exposure of the cells to the test atmosphere, the culture of cells exposed to the test atmosphere can be compared to a culture of cells that have not been exposed to a test atmosphere or to a culture of cells that is exposed to a control atmosphere—such as an atmosphere that does not contain the test atmosphere. According to this embodiment, a difference between the culture of cells exposed to the test atmosphere and the culture of cells not exposed to the test atmosphere or a difference between the culture of cells exposed to the test atmosphere and a culture of cells exposed to a control atmosphere—such as an atmosphere that does not contain the test atmosphere—is indicative that the test atmosphere effects the culture of cells.

Another aspect relates to a method for simulating the interaction between a test atmosphere and a simulated respiratory tract in the system described herein comprising: (a) with the first valve of the first pump open and the second valve of the first pump closed, providing a gas comprising a test atmosphere to the first pump via the first port; (b) closing the first valve and opening the second valve of the first pump and closing the valves on the piston plate of the first pump; (c) operating the second pump to draw the test atmosphere into the connecting structure and flushing the chamber of the first pump and the connecting structure with surrounding air; (d) opening the first valve of the first pump towards the surrounding air and forming a sealed connection between the first port and the second port of the first pump; and (e) after a period of time using the second pump to displace the test atmosphere through the connecting structure and through the first valve of the first pump.

Another aspect relates to a method for determining the effect of a test atmosphere on a simulated respiratory tract in the system described herein comprising: (a) with the first valve of the first pump open and the second valve of the first pump closed, providing a gas comprising a test atmosphere to the first pump via the first port; (b) closing the first valve and opening the second valve of the first pump and closing the valves on the piston plate of the first pump; (c) operating the second pump to draw the test atmosphere through the connecting structure and flushing the chamber of the first pump and the connecting structure with surrounding air; (d) opening the first valve of the first pump towards the surrounding air and forming a sealed connection between the first port and the second port of the first pump; and (e) after a period of time using the second pump to displace the test atmosphere through the connecting structure and through the first valve of the first pump; wherein the test atmosphere contacts a cell culture located in one or more modules located in the first pump or the connecting structure or the second pump or a combination of two or more thereof and said method comprises the further step of determining the effect of the test atmosphere on the cell culture, wherein a difference in the cell culture before and/or after exposure to the test atmosphere is indicative that the test atmosphere effects the cell culture.

In the embodiment where a difference between the culture of cells is determined after exposure of the cells to the test atmosphere, the culture of cells exposed to the test atmosphere can be compared to a culture of cells that have not been exposed to a test atmosphere or to a culture of cells that is exposed to a control atmosphere—such as an atmosphere that does not contain the test atmosphere. According to this embodiment, a difference between the culture of cells exposed to the test atmosphere and the culture of cells not exposed to the test atmosphere or a difference between the culture of cells exposed to the test atmosphere and a culture of cells exposed to a control atmosphere—such as an atmosphere that does not contain the test atmosphere—is indicative that the test atmosphere effects the culture of cells.

A further aspect relates to a method for simulating the interaction between a test atmosphere and a simulated respiratory tract comprising: (a) providing a test atmosphere to a chamber of a first pump; (b) withdrawing the test atmosphere from the first pump into a connecting structure that joins the first pump to a second pump; (c) flushing the first pump and at least of a portion of the connecting structure with surrounding air; (d) holding the test atmosphere in the second pump and the connecting structure for a defined period of time; (e) displacing the test atmosphere into the connecting structure and the first pump using the second pump; and (f) performing one or more pumping cycles of the surrounding air in the second pump; wherein the test atmosphere contacts a cell culture located in the first pump or the connecting structure or the second pump or a combination of two or more thereof.

A further aspect relates to a method for determining the effect of a test atmosphere on a simulated respiratory tract comprising: (a) providing a test atmosphere to a chamber of a first pump; (b) withdrawing the test atmosphere from the first pump into a connecting structure that joins the first pump to a second pump; (c) flushing the first pump and at least of a portion of the connecting structure with surrounding air; (d) holding the test atmosphere in the second pump and the connecting structure for a defined period of time; (e) displacing the test atmosphere through the connecting structure and the first pump using the second pump; and (f) performing one or more pumping cycles of the surrounding air in the second pump; wherein the test atmosphere contacts a cell culture located in one or more modules located in the first pump or the connecting structure or the second pump or a combination of two or more thereof and said method comprises the further step of determining the effect of the test atmosphere on the cell culture, wherein a difference in the cell culture before and/or after exposure to the test atmosphere is indicative that the test atmosphere effects the cell culture. In the embodiment where a difference between the culture of cells is determined after exposure of the cells to the test atmosphere, the culture of cells exposed to the test atmosphere can be compared to a culture of cells that have not been exposed to a test atmosphere or to a culture of cells that is exposed to a control atmosphere—such as an atmosphere that does not contain the test atmosphere. According to this embodiment, a difference between the culture of cells exposed to the test atmosphere and the culture of cells not exposed to the test atmosphere or a difference between the culture of cells exposed to the test atmosphere and a culture of cells exposed to a control atmosphere—such as an atmosphere that does not contain the test atmosphere—is indicative that the test atmosphere effects the culture of cells.

The effect of the test atmosphere(s) may be studied in the presence of one or more agents. The agent(s) can include, but are not limited to, a drug, a toxin, a pathogen, a protein, a nucleic acid, an antigen, an antibody, and a chemical compound etc. Examples of the effects that can be measured include consumption of oxygen, production of carbon dioxide, cell viability, expression of a protein, enzyme activity, penetration, permeability barrier function, surfactant production, response to cytokines, transporter function, cytochrome P450 expression, albumin secretion, toxicology and the like.

A plurality of assays may be run in parallel with different concentrations of the test atmosphere and/or agent to obtain a differential response to the various concentrations.

The agent may be any test compound of interest and includes small organic compounds, polypeptides, peptides, higher molecular weight carbohydrates, polynucleotides, fatty acids and lipids, aerosol or one or more components of an aerosol and the like. Test compounds may be screened individually or in sets or combinatorial libraries of compounds. Test compounds can be obtained from a wide variety of sources including libraries of synthetic or natural compounds. Libraries of natural compounds in the form of bacterial, fungal, plant and animal extracts can be used. Natural or synthetically produced libraries and compounds that are modified through conventional chemical, physical and biochemical means may be used to produce combinatorial libraries. Known pharmacological agents may be subjected to directed or random chemical modifications, such as acylation, alkylation, esterification, acidification to produce structural analogues for screening.

One or more variables that can be measured include elements of cells, subcellular material, subcellular components, or cellular products. By way of example, the toxicology of the test atmosphere can be measured. The aerosol dynamics in the respiratory tract (e.g. aerosol particle deposition and absorption of gases into cell cultures) can be measured. By way of further example, the metabolic activity and/or the transport of molecules across the epithelia of the respiratory tract can be studied.

Computer

There is also disclosed a computer program which when executed by a computer/processor is operable to control the computer to perform one or more of the methods described herein.

A person of skill in the art will readily recognize that steps of various of the above-described methods can be performed by programmed computers. Herein, some embodiments are also intended to cover program storage devices, for example, digital data storage media, which are machine or computer readable and encode machine-executable or computer-executable programs of instructions, wherein said instructions perform some or all of the steps of said above-described methods. The program storage devices may be, for example, digital memories, magnetic storage media such as a magnetic disks and magnetic tapes, hard drives, or optically readable digital data storage media. The embodiments are also intended to cover computers programmed to perform some or all of the steps of the above-described methods.

The functions of the various elements including the processors or logic, may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" or "logic" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non-volatile storage. Other hardware, conventional and/or custom, may also be included. Similarly, any switches shown in the Figures are conceptual only. Their function may be carried out through the operation of program logic, through dedicated logic, through the interaction of program control and dedicated logic, or even manually, the particular technique being selectable by the implementer as more specifically understood from the context.

Further aspects of the disclosure as set forth in the following numbered paragraphs:

1. A system for determining the interaction between a test atmosphere and a simulated respiratory tract, said system comprising: (a) a first pump comprising: (i) a chamber configured for containing a first volume of gas comprising a test atmosphere; (ii) a first port adapted for receiving and outputting gas and comprising a valve for regulating the flow of gas through the first port, said valve being moveable between open and closed positions, wherein in the open position said valve is openable towards a test atmosphere or surrounding air; (iii) a second port adapted for outputting and receiving gas and comprising a valve for regulating the flow of gas through the second port, said valve being moveable between open and closed positions; (iv) a piston plate containing a plurality of openings therein, wherein one or more of the openings comprise valves adapted for regulating the flow of gas through the openings; and (v) a motor for controlling the operation of the first pump; (b) a second pump comprising: (i) a chamber configured for containing a second volume of gas, wherein the first and second volumes of gas are different; (ii) a port adapted for receiving and outputting gas; and (iii) a motor for controlling the operation of the second pump; (c) a connecting structure operable to transmit the gas from the first pump into the second pump; and (d) one or more openings in the first pump or the second pump or the walls of the connecting structure or a combination of two or more thereof, said openings being capable of receiving a module for containing a cell culture medium or configured to store a cell culture medium or for monitoring conditions in the chamber or adapted to monitor conditions in the chamber or for gas sampling or adapted to sample gas or for gas characterisation or adapted to characterise gas.
2. The system according to paragraph 1, wherein the pumps are piston pumps comprising a piston plate and a base.
3. The system according to paragraph 1 or paragraph 1, wherein the connecting structure is hollow.
4. The system according to any of the preceding paragraphs, wherein the connecting structure is branched.
5. The system according to paragraph 4, wherein one terminating branch of the connecting structure is joined to the second pump and one or more further terminating branches are joined to a separate pump, each separate pump comprising: (i) a chamber to contain a volume of gas, wherein the volume of gas is the same volume as the second volume of gas in the second pump; (ii) a port for receiving and outputting gas and for joining to the connecting structure; and (iii) a motor for controlling the operation of the pump.
6. The system according to paragraph 5, wherein each separate pump is the same as the second pump.
7. The system according to any of the preceding paragraphs, wherein the system is contained in a housing, suitably a temperature controlled housing.
8. The system according paragraph 7, wherein the temperature of the housing is controlled by a thermostat.
9. The system according to paragraph 8, wherein the temperature in the housing is about 37° C.
10. The system according to any of the preceding paragraphs, wherein the different volumes of the first and second pumps represent the internal volume of different compartments of the respiratory tract, suitably, the human respiratory tract.
11. The system according to any of paragraphs 6 to 10, wherein the volume of the separate pumps represent the internal volume of different compartments of the respiratory tract, suitably, the human respiratory tract.
12. The system according to any of the preceding paragraphs, wherein the displacement volume of the first and second pumps is at least as large as the maximally achievable volume uptake in the corresponding compartment of the respiratory tract.
13. The system according to any of paragraphs 5 to 12, wherein the displacement volume of the separate pumps is at least as large as the maximally achievable volume uptake in the corresponding compartment of the respiratory tract.
14. The system according to any of the preceding paragraphs, wherein the pumping pressure of the motor or pump can correspond to atmospheric pressure or above or below atmospheric pressure.
15. The system according to any of the preceding paragraphs, wherein the displacement volume of the first pump is between about 0 and 100 ml or between about 1 and 100 ml.
16. The system according to any of the preceding paragraphs, wherein the displacement volume of the second pump is between about 0 and 4000 ml or between about 1 and about 4000 ml.
17. The system according to any of the preceding paragraphs, wherein the pumps comprise or consist of stainless steel.
18. The system according to any of the preceding paragraphs, wherein the chamber is a cylinder.
19. The system according to any of the preceding paragraphs, wherein the chamber comprises glass.
20. The system according to any of the preceding paragraphs, wherein the chamber of the first pump has a smaller volume than the chamber of the second pump.
21. The system according to any of the preceding paragraphs, wherein the volume of the chamber of the first pump represents the volume of the oral and oropharyngeal cavity.
22. The system according to any of the preceding paragraphs, wherein the volume of the chamber of the second pump represents the volume of lung lumen or a part thereof.
23. The system according to any of the preceding paragraphs, wherein the volume of the connecting structure represents the volume of conducting airways of the lung, suitably the human lung.

24. The system according to any of the preceding paragraphs, wherein the piston plate of the first pump comprises one or more apertures for the uptake or inflow of gas.
25. The system according to any of the preceding paragraphs, wherein the one or more apertures each include a valve that is movable between open and closed positions and is capable of regulating the uptake or inflow of gas.
26. The system according to any of the preceding paragraphs, wherein the system further comprises a computer controller capable of synchronising the operation of the system.
27. The system according to any of the preceding paragraphs, wherein one or more of the first pump or the second pump or the connecting structure comprise one or more modules containing quartz crystal microbalances.
28. The system according to any of the preceding paragraphs, wherein the openings in the first pump or the second pump or the walls of the connecting structure are threaded or non-threaded.
29. The system according to any of the preceding paragraphs, wherein one or more of the openings contain a module.
30. The system according to paragraph 29, wherein the one or more modules are adapted to contain a cell culture medium or configured to store a cell culture medium or adapted to monitor conditions in the chamber or adapted to monitor conditions in the chamber or adapted to sample gas or adapted to characterise gas.
31. The system according to paragraph 29 or 30, wherein the modules are located on the base of the piston plate of the first and/or second pump and/or in the walls of the connecting structure.
32. The system according to any of paragraphs 29 to 31, wherein the one or more modules contain a cell culture medium.
33. The system according to any of the preceding paragraphs, wherein the cell culture medium comprises or is in contact with a culture of cells, suitably, a 2- or 3-dimensional culture of cells.
34. The system according to any of paragraphs 29 to 32, wherein the modules adapted for containing or storing a cell culture medium further comprise a microfluidic channel and optionally a microfluidic pump connected thereto.
35. The system according to any of paragraphs 29 to 34, wherein the modules are positioned in a horizontal plane in one or more of the first pump or the second pump or the walls of the connecting structure.
36. The system according to any of the preceding paragraphs, wherein the connecting structure comprises stainless steel.
37. The system according to any of the preceding paragraphs, wherein the chamber of the first pump has a volume of about 100 ml.
38. The system according to any of the preceding paragraphs, wherein the chamber of the second pump has a volume of about 1 litre to about 4 litres.
39. A pump for displacing a volume of gas comprising: (i) a chamber configured for containing a volume of gas and comprising a base and one or more openings capable of receiving one or more modules for containing or storing a cell culture medium or for monitoring conditions in the chamber or for gas sampling or for gas characterisation; (ii) a first port for receiving and outputting the gas, when contained in the chamber, and comprising a first valve for regulating the flow of gas through the first port, said first valve being moveable between open and closed positions, wherein in the open position said valve can be opened towards a test atmosphere or surrounding air; and (iii) a second port for outputting and receiving gas, when contained in the chamber, and comprising a second valve for regulating the flow of gas through the second port, said valve being moveable between open and closed positions; and (iv) a piston plate containing a plurality of openings therein, wherein one or more of the openings comprise valves adapted for regulating the flow of gas through the openings.
40. The pump according to paragraph 39, wherein the pump is a piston pump comprising a piston plate.
41. The pump according to paragraph 39 or 40, wherein the one or more openings in the chamber are threaded or non-threaded.
42. The pump according to any of paragraphs 39 to 41, wherein the one or more openings comprise a module.
43. The pump according to paragraph 42, wherein the module is threaded or non-threaded.
44. The pump according to paragraph 42 or 43, wherein the one or more modules are adapted to contain a cell culture medium or configured to store a cell culture medium or adapted to monitor conditions in the chamber or adapted to monitor conditions in the chamber or adapted to sample gas or adapted to characterise gas.
45. The pump according to any of paragraphs 42 to 44, wherein the modules are located on the base of the pump.
46. The pump according to any of paragraphs 42 to 45, wherein the one or modules contain a cell culture medium.
47. The pump according to paragraph 46, wherein the cell culture medium comprises or is in contact with a culture of cells, suitably, a 2 or 3-dimensional culture of cells.
48. The pump according to any of paragraphs 44 to 47, wherein the modules adapted for containing or storing a cell culture medium further comprise a microfluidic channel and optionally a microfluidic pump connected thereto.
49. The pump according to any of paragraphs 42 to 48, wherein the modules are positioned in a horizontal plane in the one or more of the first pump or the second pump or the walls of the connecting structure.
50. The pump according to any of paragraphs 43 to 49, wherein the module comprises quartz crystal microbalances.
51. The pump according to any of paragraphs 39 to 50, wherein the pump further comprises a motor.
52. The pump according to any of paragraphs 39 to 51, wherein the pumping pressure corresponds to atmospheric pressure or above or below atmospheric pressure.
53. The pump according to any of paragraphs 39 to 52, wherein the displacement volume of the pump is between about 0 and 100 ml or between about 1 and about 100 ml.
54. The pump according to any of paragraphs 39 to 53, wherein the pump comprises stainless steel.
55. The pump according to any of paragraphs 39 to 54, wherein the chamber is a cylinder.

56. The pump according to any of paragraphs 39 to 55, wherein the chamber comprises glass.
57. The pump according to any of paragraphs 39 to 56, wherein the chamber of the pump has a volume of about 100 ml.
58. The pump according to any of paragraphs 39 to 57, wherein the piston plate of the pump comprises one or more apertures for the uptake or inflow of gas.
59. The pump according to paragraph 58, wherein the one or more of the apertures include a valve that is movable between open and closed positions and is capable of regulating the uptake or inflow of gas.
60. A piston pump for displacing a volume of gas comprising: (i) a chamber configured for containing a volume of gas and containing a piston plate comprising one or more apertures for the uptake or inflow of gas into the chamber, wherein one or more, or each, of the apertures include a valve that is movable between open and closed positions and is capable of regulating the uptake or inflow of gas; (ii) a first port for receiving the gas and comprising a first valve for regulating the flow of gas through the first port, said first valve being moveable between open and closed positions; and (iii) a second port for outputting gas, when contained in the chamber, and comprising a second valve for regulating the flow of gas through the second port, said valve being moveable between open and closed positions.
61. The pump according to paragraph 60, wherein the chamber includes a base and comprises one more openings.
62. The pump according to paragraph 61, wherein the openings are threaded or non-threaded.
63. The pump according to paragraph 60 or 61, wherein the openings comprise a module in one or more of the openings.
64. The pump according to paragraph 63, wherein the module is threaded or non-threaded.
65. The pump according to paragraph 63 or 64, wherein the module is adapted for containing or storing a cell culture medium or for monitoring conditions in the chamber or for gas sampling or for gas characterisation.
66. The pump according to any of paragraphs 63 to 65, wherein the one or modules contain a cell culture medium.
67. The pump according to paragraph 66, wherein the cell culture medium comprises a culture of cells, suitably, a 2- or 3-dimensional culture of cells.
68. The pump according to any of paragraphs 63 to 67, wherein the modules adapted for containing or storing a cell culture medium further comprise a microfluidic channel and optionally a microfluidic pump connected thereto.
69. The pump according to any of paragraphs 63 to 67, wherein the module comprises quartz crystal microbalances.
70. The pump according to any of paragraphs 60 to 69, wherein a connecting structure is joined to the second port.
71. The pump according to any of paragraph 70, wherein the connecting structure is hollow. Suitably, the pump further comprises a motor.
72. The pump according to any of paragraphs 60 to 71, wherein the pumping pressure of the pump corresponds to atmospheric pressure or above or below atmospheric pressure.
73. The pump according to any of paragraphs 60 to 72, wherein the displacement volume of the pump is between about 0 and 100 ml or between about 1 and about 100 ml.
74. The pump according to any of paragraphs 60 to 73, wherein the pump comprises stainless steel.
75. The pump according to any of paragraphs 60 to 74, wherein the chamber is a cylinder.
76. The pump according to any of paragraphs 60 to 75, wherein the chamber comprises glass.
77. The pump according to any of paragraphs 60 to 76, wherein the chamber of the pump has a volume of about 100 ml.
78. A pump for displacing a volume of gas comprising: (i) a chamber configured for containing a volume of gas, said chamber comprising a base and one or more modules for containing or storing a cell culture medium or for monitoring conditions in the chamber or for gas sampling or for gas characterisation; and (ii) a port operable for receiving and outputting the gas.
79. The pump according to paragraph 78, wherein the pump is a piston pump comprising a piston plate.
80. The pump according to paragraph 79, wherein, the piston plate is free of any apertures or openings.
81. The pump according to any of paragraphs 78 to 80, wherein the modules are located in the base of the chamber.
82. The pump according to any of paragraphs 78 to 81, wherein the modules are threaded or non-threaded.
83. The pump according to any of paragraphs 78 to 82, wherein the modules are adapted to contain a cell culture medium or configured to store a cell culture medium or adapted to monitor conditions in the chamber or adapted to monitor conditions in the chamber or adapted to sample gas or adapted to characterise gas.
84. The pump according to any of paragraphs 78 to 83, wherein the one or modules contain a cell culture medium.
85. The pump according to paragraph 84, wherein the cell culture medium comprises or is in contact with a culture of cells, suitably, a 2- or 3-dimensional culture of cells.
86. The pump according to paragraph 84 or 85, wherein the modules adapted for containing or storing a cell culture medium further comprise a microfluidic channel and optionally a microfluidic pump connected thereto.
87. The pump according to any of paragraphs 78 to 82, wherein the module comprises quartz crystal microbalances.
88. The pump according to any of paragraphs 78 to 87, wherein a connecting structure is joined to the port.
89. The pump according to any of paragraphs 78 to 88, wherein the connecting structure is hollow.
90. The pump according to any of paragraphs 78 to 89, wherein the pump further comprises a motor.
91. The pump according to any of paragraphs 78 to 90, wherein the pumping pressure corresponds to atmospheric pressure or above or below atmospheric pressure.
92. The pump according to any of paragraphs 78 to 91, wherein the displacement volume of the pump is between about 0 and 1000 ml or between about 1 and about 100 ml.
93. The pump according to any of paragraphs 78 to 92, wherein the pump comprises stainless steel.

94. The pump according to any of paragraphs 78 to 93, wherein the chamber is a cylinder.
95. The pump according to any of paragraphs 78 to 94, wherein the chamber comprises glass.
96. The pump according to any of paragraphs 78 to 95, wherein the volume of the chamber represents the volume of lung lumen or a part thereof.
97. A connecting structure adapted for joining at least two pumps for transmitting a gas there between, said connecting structure comprising a hollow channel and or more threaded or non-threaded openings in the walls of the connecting structure.
98. The connecting structure according to paragraph 97, wherein the threaded openings contain a threaded module in one or more of the openings, said module being adapted to contain a cell culture medium or configured to store a cell culture medium or adapted to monitor conditions in the chamber or adapted to monitor conditions in the chamber or adapted to sample gas or adapted to characterise gas.
99. The connecting structure according to paragraph 98, wherein the one or modules contain a cell culture medium.
100. The connecting structure according to paragraph 99, wherein the cell culture medium comprises or is in contact with a culture of cells, suitably, a 2- or 3-dimensional culture of cells.
101. The connecting structure according to any of paragraphs 98 to 100, wherein the modules adapted for containing or storing a cell culture medium further comprise a microfluidic
102. The connecting structure according to any of paragraphs 97 to 102, wherein a channel and optionally a microfluidic pump are connected thereto.
103. The connecting structure according to any of paragraphs 97 to 102, wherein the connecting structure is hollow.
104. The connecting structure according to any of paragraphs 97 to 103, wherein the connecting structure is branched.
105. The connecting structure according to paragraph 104, wherein each terminating branch of the connecting structure is capable of being joined to a separate pump.
106. The connecting structure according to any of paragraphs 97 to 105, wherein the connecting structure represents the volume of conducting airways of the lung, suitably the human lung.
107. The connecting structure according to any of paragraphs 98 to 106, wherein the modules are positioned in a horizontal plane in the walls of the connecting structure.
108. The connecting structure according to any of paragraphs 98 to 107, wherein the modules are adapted to contain a culture of cells, suitably, a 2- or 3-dimensional culture of cells.
109. The connecting structure according to any of paragraphs 98 to 108, wherein the module is a chamber for containing a culture of cells, said chamber comprising a microfluidic channel and optionally a microfluidic pump connected thereto.
110. The connecting structure according to any of paragraphs 98 to 103, wherein the modules are adapted for monitoring conditions in the connecting structure and/or for gas sampling and/or for gas characterisation.
111. The connecting structure according to any of paragraphs 97 to 110, wherein the connecting structure comprises stainless steel.
112. A system comprising the pumps one or more of the pumps as defined in any of paragraphs 39 to 96.
113. The system according to paragraph 112, wherein the system further comprises the connecting structure as defined in any of paragraphs 97 to 111.
114. The system according to paragraph 112 or paragraph 112, wherein the pumps are joined by the connecting structure.
115. A method for simulating the interaction between a test atmosphere and a simulated respiratory tract comprising the use of the system according to any of paragraphs 1 to 38.
116. Use of the system according to any of paragraphs 1 to 38 for simulating the interaction between a test atmosphere and a simulated respiratory tract.
117. A method for determining the effect of a test atmosphere on a culture of cells contained in a simulated respiratory tract comprising the use of the system according to any of paragraphs 1 to 38.
118. Use of the system according to any of paragraphs 1 to 38 for determining the effect of a test atmosphere on a culture of cells contained in a simulated respiratory tract
119. A method for determining the effect of a test atmosphere on a culture of cells contained in a simulated respiratory tract comprising: (a) providing the system as described herein, wherein the system contains a culture of cells in one or more of the modules; and (b) comparing the culture of cells before and/or after exposure to the test atmosphere, wherein a difference between the culture of cells before and/or after exposure of the cells to the test atmosphere is indicative that the test atmosphere effects the culture of cells.
120. A method for simulating the interaction between a test atmosphere and a simulated respiratory tract in the system described herein comprising: (a) with the first valve of the first pump open and the second valve of the first pump closed, providing a gas comprising a test atmosphere to the first pump via the first port; (b) closing the first valve and opening the second valve of the first pump and closing the valves on the piston plate of the first pump; (c) operating the second pump to draw the test atmosphere into the connecting structure and flushing the chamber of the first pump and the connecting structure with surrounding air; (d) opening the first valve of the first pump towards the surrounding air and forming a sealed connection between the first port and the second port of the first pump; and (e) after a period of time using the second pump to displace the test atmosphere through the connecting structure and through the first valve of the first pump.
121. A method for determining the effect of a test atmosphere on a simulated respiratory tract in the system described herein comprising: (a) with the first valve of the first pump open and the second valve of the first pump closed, providing a gas comprising a test atmosphere to the first pump via the first port; (b) closing the first valve and opening the second valve of the first pump and closing the valves on the piston plate of the first pump; (c) operating the second pump to draw the test atmosphere through the connecting structure and flushing the chamber of the first pump and the connecting structure with surrounding air; (d) opening the first valve of the first pump towards the surrounding air and forming a sealed connection between the first port and the second port of the first pump; and (e) after a period of time using the second pump to displace the test atmosphere through the connecting structure and through the first valve of the first pump; wherein the test atmosphere contacts a cell culture located in one or more modules located in the first pump or the connecting structure or the second pump or a combination of two or more thereof and said method comprises the further step of determining the effect of the test atmosphere on the cell culture, wherein a difference in the cell culture before and/or after exposure to the test atmosphere is indicative that the test atmosphere effects the cell culture.

122. The method of paragraph 121, wherein the modules are adapted to monitor system conditions and/or for gas sampling and/or for gas characterisation and said method comprises taking one or more measurements from the modules.

123. A method for simulating the interaction between a test atmosphere and a simulated respiratory tract comprising: (a) providing a test atmosphere to a chamber of a first pump; (b) withdrawing the test atmosphere from the first pump into a connecting structure that joins the first pump to a second pump; (c) flushing the first pump and at least of a portion of the connecting structure with surrounding air; (d) holding the test atmosphere in the second pump and the connecting structure for a defined period of time; (e) displacing the test atmosphere into the connecting structure and the first pump using the second pump; and (f) performing one or more pumping cycles of the surrounding air in the second pump; wherein the test atmosphere contacts a cell culture located in the first pump or the connecting structure or the second pump or a combination of two or more thereof.

124. The method according to paragraph 123, wherein step (d) comprises holding the test atmosphere in the second pump and the portion of the connecting structure still containing test atmosphere for a defined period of time.

125. The method according to paragraph 123 or 124, wherein the pumps are piston pumps comprising a piston plate and a base.

126. The method according to any of paragraphs 123 to 125, wherein the first pump is as defined in any of paragraphs 39 to 77.

127. The method according to any of paragraphs 123 to 126, wherein the second pump is as defined in any of paragraphs 78 to 96.

128. The method according to any of paragraphs 123 to 127, wherein the connecting structure is as defined in any of paragraph 97 to 111.

129. The method according to any of paragraphs 123 to 128, wherein the method is performed in a housing, suitably a temperature controlled housing.

130. The method according to any of paragraphs 123 to 129, wherein the temperature of the housing is controlled by a thermostat.

131. The method according to any of paragraphs 123 to 130, wherein the temperature in the housing is about 37° C.

132. The method according to any of paragraphs 123 to 131, wherein the different volumes of the first and second pumps represent the internal volume of different compartments of the respiratory tract, suitably, the human respiratory tract.

133. The method according to any of paragraphs 123 to 132, wherein the displacement volume of the first and second pumps is at least as large as the maximally achievable volume uptake in the corresponding compartment of the respiratory tract.

134. The method according to any of paragraphs 123 to 133, wherein the pumping pressure corresponds to atmospheric pressure or above or below atmospheric pressure.

135. The method according to any of paragraphs 123 to 134, wherein the displacement volume of the first pump is between about 0 and 100 ml or between about 1 and about 100 ml.

136. The method according to any of paragraphs 123 to 135, wherein the displacement volume of the second pump is between about 0 and 4000 ml or between about 1 and about 4000 ml.

137. The method according to any of paragraphs 123 to 136, wherein the chamber of the first pump has a smaller volume than the chamber of the second pump.

138. The method according to any of paragraphs 123 to 137, wherein the volume of the chamber of the first pump represents the volume of the oral and oropharyngeal cavity, suitably the human oral and oropharyngeal cavity.

139. The method according to any of paragraphs 123 to 138, wherein the volume of the chamber of the second pump represents the volume of lung lumen or a part thereof, suitably, the human lung lumen or a part thereof.

140. The method according to any of paragraphs 123 to 139, wherein the connecting structure represents the volume of conducting airways of the lung, suitably the human lung.

141. The method according to any of paragraphs 123 to 140, wherein the piston plate comprises one or more apertures for the uptake or inflow of gas into the chamber.

142. The method according to any of paragraphs 123 to 141, wherein the one or more apertures each include a valve that is movable between open and closed positions and is capable of regulating the uptake or inflow of gas.

143. The method according to any of paragraphs 123 to 142, wherein the culture of cells is located on the base of the piston plate of the first and/or second pump and/or in the walls of the connecting structure.

143. The method according to any of paragraphs 122 to 142, wherein the culture of cells is a 2- or 3-dimensional culture.

144. The method according to any of paragraphs 122 to 143, wherein the method further comprises monitoring conditions and/or for gas sampling and/or for gas characterisation and in one or more of the first pump or the second pump or the connecting structure using one or more modules contained therein.

145. The method according to any of paragraphs 122 to 144, wherein the chamber comprising the culture of cells further comprises a microfluidic channel and optionally a microfluidic pump connected thereto.

145. The method according to any of paragraphs 122 to 145, wherein the connecting structure comprises stainless steel.

146. The method according to any of paragraphs 122 to 145, wherein the chamber of the first pump has a volume of about 100 ml.

147. The method according to any of paragraphs 122 to 146, wherein the chamber of the second pump has a volume of about 1 litre to about 4 litres.

148. A method for determining the effect of a test atmosphere on a simulated respiratory tract comprising: (a) providing a test atmosphere to a chamber of a first pump; (b) withdrawing the test atmosphere from the first pump into a connecting structure that joins the first pump to a second pump; (c) flushing the first pump and at least of a portion of the connecting structure with surrounding air; (d) holding the test atmosphere in the second pump and the connecting structure for a defined period of time; (e) displacing the test atmosphere through the connecting structure and the first pump using the second pump; and (f) performing one or more pumping cycles of the surrounding air in the second pump; wherein the test atmosphere contacts a cell culture located in one or more modules located in the first pump or the connecting structure or the second pump or a combination of two or more thereof and said method comprises the further step of determining the effect of the test atmosphere on the cell culture, wherein a difference in the cell culture before and/or after exposure to the test atmosphere is indicative that the test atmosphere effects the cell culture.

149. The method according to paragraph 148, wherein the modules are adapted to monitor system conditions and/or for gas sampling and/or for gas characterisation and said method comprises taking one or more measurements from the modules.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant art are intended to be within the scope of the following claims.

The invention claimed is:

1. A system for determining the interaction between a test atmosphere and a simulated respiratory tract, said system comprising:

(a) a first pump comprising:
  (i) a chamber configured for containing a first volume of gas comprising a test atmosphere;
  (ii) a first port adapted for receiving and outputting gas and comprising a valve for regulating the flow of gas through the first port, said valve being moveable between open and closed positions, wherein in the open position said valve is openable towards a test atmosphere or surrounding air;
  (iii) a second port adapted for outputting and receiving gas and comprising a valve for regulating the flow of gas through the second port, said valve being moveable between open and closed positions;
  (iv) a piston plate in the chamber, said piston plate comprising one or more apertures for the uptake or inflow of gas into the chamber wherein one or more, or each, of the apertures include a valve that is movable between open and closed positions and is capable of regulating the uptake or inflow of gas; and
  (v) a motor for controlling the operation of the first pump;
(b) a second pump comprising:
  (i) a chamber configured for containing a second volume of gas, wherein the first and second volumes of gas are different;
  (ii) a port adapted for receiving and outputting gas; and
  (iii) a motor for controlling the operation of the second pump;
(c) a connecting structure operable to transmit the gas from the first pump into the second pump; and
(d) one or more openings in the first pump or the second pump or the walls of the connecting structure or a combination of two or more thereof, said one or more openings being capable of receiving a module for containing a cell culture medium or for monitoring conditions in the chamber or for gas sampling or for gas characterization.

2. Use of the system according to claim 1 for simulating the interaction between a test atmosphere and a simulated respiratory tract.

3. The system of claim 1, wherein the one or more openings in the first pump or the second pump are located on a base of the chamber of the pump.

4. The system of claim 1, wherein the first pump and/or second pump is a piston pump comprising the piston plate and a base.

5. The system of claim 1, wherein the system is contained in a housing.

6. The system of claim 5, wherein the housing is a temperature-controlled housing.

7. The system of claim 1, wherein the chamber of the first pump has a smaller volume than the chamber of the second pump.

8. The system of claim 1, wherein the system further comprises a computer controller configured to synchronize operation of the system.

9. The system of claim 1, wherein the one or more openings contain a module.

10. The system of claim 9, wherein the module is located on a base of the piston plate of the first and/or second pump.

* * * * *